(12) United States Patent
Weber et al.

(10) Patent No.: US 11,622,882 B1
(45) Date of Patent: *Apr. 11, 2023

(54) MOBILE COLD THERAPY DEVICE

(71) Applicant: EVOLVE ORTHOPEDICS LLC, Santa Barbara, CA (US)

(72) Inventors: James J. Weber, Santa Barbara, CA (US); Gary Walters, Escondido, CA (US)

(73) Assignee: EVOLVE ORTHOPEDICS LLC, Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/706,430

(22) Filed: Mar. 28, 2022

Related U.S. Application Data

(63) Continuation-in-part of application No. 17/401,073, filed on Aug. 12, 2021, now Pat. No. 11,285,037.

(60) Provisional application No. 63/065,382, filed on Aug. 13, 2020.

(51) Int. Cl.
    *A61F 7/00* (2006.01)
    *A61H 9/00* (2006.01)

(52) U.S. Cl.
    CPC .... *A61F 7/0085* (2013.01); *A61F 2007/0056* (2013.01); *A61F 2007/0091* (2013.01); *A61F 2007/0093* (2013.01); *A61H 9/0078* (2013.01)

(58) Field of Classification Search
    CPC ............ A61F 7/0085; A61F 2007/0056; A61F 2007/0091
    See application file for complete search history.

(56) References Cited

U.S. PATENT DOCUMENTS

| | | |
|---|---|---|
| 4,470,263 A | 9/1984 | Lehovec et al. |
| 5,080,089 A | 1/1992 | Mason et al. |
| 5,232,020 A | 8/1993 | Mason et al. |
| 5,241,951 A | 9/1993 | Mason et al. |
| 5,330,519 A | 7/1994 | Mason et al. |
| 5,417,720 A | 5/1995 | Mason |
| 5,507,792 A | 4/1996 | Mason et al. |
| 5,647,051 A | 7/1997 | Neer |
| 6,023,932 A | 2/2000 | Johnston |

(Continued)

FOREIGN PATENT DOCUMENTS

| | | |
|---|---|---|
| WO | WO2015/106317 A1 | 7/2015 |

OTHER PUBLICATIONS

Breg, "VPULSE User's Manual," 2019, pp. 1-24, Breg, Inc., Carlsbad, CA.

(Continued)

*Primary Examiner* — Kaitlyn E Smith
(74) *Attorney, Agent, or Firm* — Paul Y. Feng; One LLP

(57) ABSTRACT

A mobile, self-contained cold therapy device having a container including an internal liquid or ice water tank, air and water pumps for driving air and water to a cold therapy pad with internal air and water bladders, wherein the pad is worn on an injured region of a user. The device includes an electronic controller for controlling air and water flow to and from the bladders, and a holder for supporting the container and worn on the user's body for portable, hands-free mobility while receiving cold therapy. Nipples are incorporated into a thermal conduction surface of the pad and reciprocated into the user's injured region by an air bladder to further reduce edema.

20 Claims, 18 Drawing Sheets

(56) References Cited

U.S. PATENT DOCUMENTS

| | | | |
|---|---|---|---|
| 6,178,562 | B1 | 1/2001 | Elkins |
| 6,438,964 | B1 | 8/2002 | Giblin |
| 6,551,348 | B1 * | 4/2003 | Blalock ............... A61F 7/0085 607/104 |
| 6,695,872 | B2 | 2/2004 | Elkins |
| 6,915,641 | B2 | 7/2005 | Harvie |
| 6,948,322 | B1 | 9/2005 | Giblin |
| 7,001,417 | B2 | 2/2006 | Elkins |
| 7,249,464 | B1 | 7/2007 | Watson |
| 7,896,910 | B2 | 3/2011 | Schirrmacher et al. |
| 7,914,563 | B2 | 3/2011 | Mason et al. |
| 7,959,657 | B1 | 6/2011 | Harsy |
| 8,001,794 | B2 | 8/2011 | Windisch |
| 8,449,589 | B1 | 5/2013 | Harsy |
| 8,454,671 | B2 * | 6/2013 | Lennox .................. A61F 7/02 607/104 |
| 8,613,762 | B2 | 12/2013 | Bledsoe |
| 8,709,058 | B1 | 4/2014 | Harsy |
| 8,715,330 | B2 | 5/2014 | Lowe et al. |
| 8,753,383 | B2 * | 6/2014 | Parish .................. A61F 7/007 607/104 |
| 9,170,059 | B2 * | 10/2015 | Johnson .................. A61F 7/02 |
| 9,180,041 | B2 | 11/2015 | Parish et al. |
| 9,402,763 | B2 | 8/2016 | Bledsoe |
| 9,433,525 | B2 | 9/2016 | Parish et al. |
| 9,566,187 | B2 | 2/2017 | Edelman et al. |
| 9,849,024 | B2 | 12/2017 | Mandel |
| 9,943,437 | B2 | 4/2018 | Lowe et al. |
| 10,045,879 | B2 | 8/2018 | Robst et al. |
| 10,299,525 | B1 | 5/2019 | Buckman |
| 10,918,513 | B2 | 2/2021 | Golden et al. |
| 11,285,037 | B1 * | 3/2022 | Weber ...................... A61F 7/02 |
| 2006/0191270 | A1 | 8/2006 | Warren |
| 2006/0235498 | A1 | 10/2006 | Mollendorf et al. |
| 2008/0046047 | A1 | 2/2008 | Jacobs |
| 2009/0306748 | A1 | 12/2009 | Mollendorf et al. |
| 2010/0106229 | A1 | 4/2010 | Gammons et al. |
| 2010/0198322 | A1 | 8/2010 | Joseph et al. |
| 2010/0281883 | A1 | 11/2010 | Romano |
| 2012/0065713 | A1 | 3/2012 | Greaves et al. |
| 2012/0172957 | A1 | 7/2012 | Dewaegenaere |
| 2013/0331914 | A1 | 12/2013 | Lee et al. |
| 2013/0333394 | A1 | 12/2013 | Chow |
| 2014/0214138 | A1 | 7/2014 | Voorhees et al. |
| 2016/0324719 | A1 | 11/2016 | Badmus et al. |
| 2016/0361196 | A1 | 12/2016 | Spence et al. |
| 2017/0267907 | A1 | 9/2017 | Knott et al. |
| 2019/0159546 | A1 | 5/2019 | Cohen et al. |
| 2020/0138665 | A1 | 5/2020 | Binversie |
| 2020/0289361 | A1 | 9/2020 | Tian et al. |

OTHER PUBLICATIONS

Web Download: www.breg.com/products/cold-therapy/devices/polar-care-wave, 2019, pp. 1-3, Breg, Inc., Carlsbad, CA.

Web Download: www.breg.com/products/cold-therapy/devices/polar-care-cub, 2019, pp. 1-6, Breg, Inc., Carlsbad, CA.

Nice Recovery Systems LLC, "NICE1 Cold + Compression Therapy System User Manual," 2019, pp. 1-28, Nice Recovery Systems LLC, Boulder, CO.

\* cited by examiner

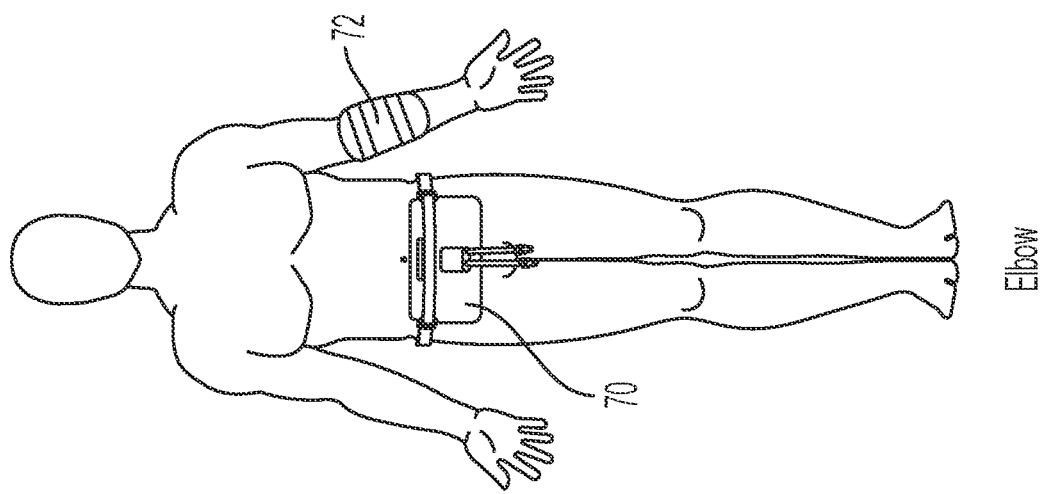
FIG. 21 Wrist
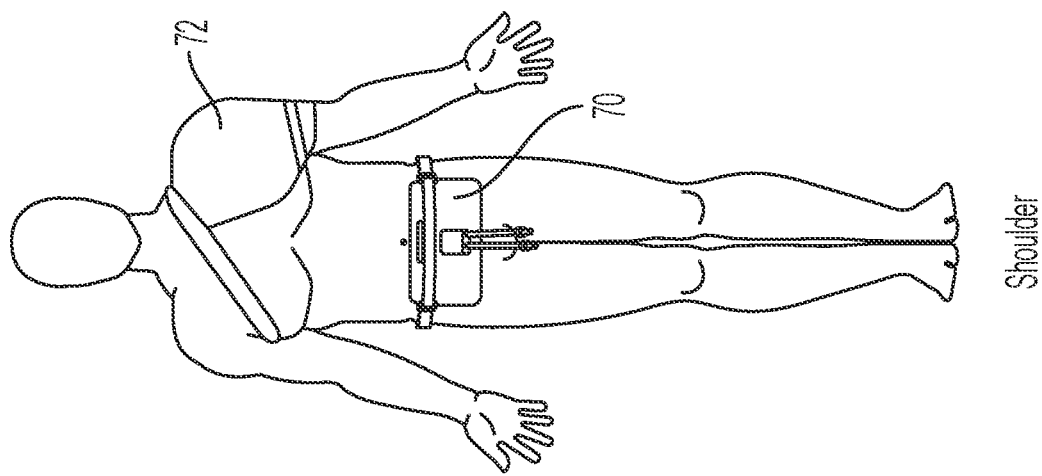
FIG. 22 Shoulder
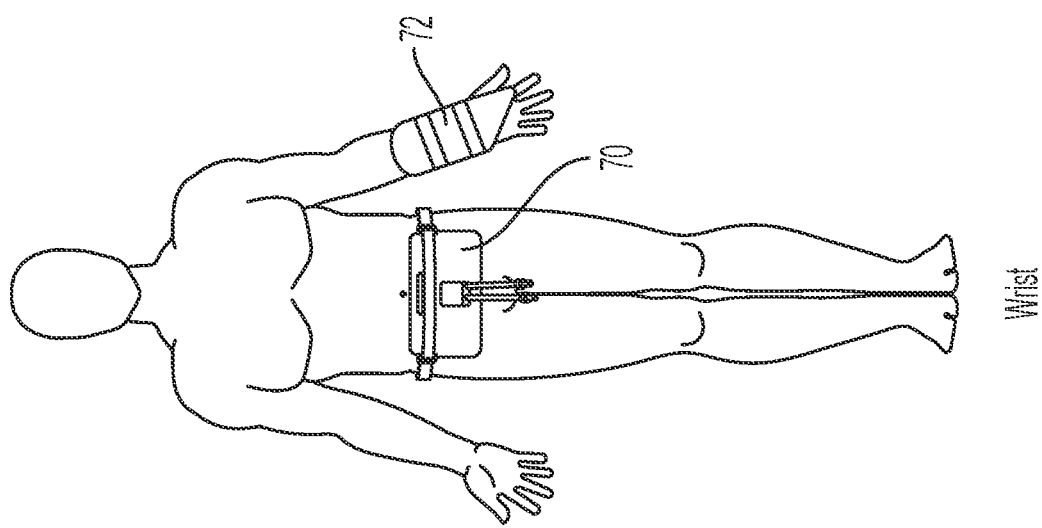
FIG. 23 Elbow

MOBILE COLD THERAPY DEVICE

CROSS-REFERENCE TO RELATED APPLICATIONS

This application is a continuation-in-part of co-pending U.S. patent application Ser. No. 17/401,073, filed Aug. 12, 2021, which claims priority to provisional patent application No. 63/065,382, filed Aug. 13, 2020, titled "Mobile Cold Therapy," the entire contents of which are hereby incorporated by reference.

FIELD OF THE INVENTION

The present invention relates generally to cold therapy devices. More particularly, the invention relates to a self-contained, mobile cold therapy device that can be worn on the body of the user leaving him or her hands-free and able to ambulate while still receiving cold therapy.

BACKGROUND

Cold therapy is often prescribed for relief and/or control of inflammation, among other ailments. Often, to apply cold therapy to a user, the options for the user are limited. Ice packs or gel packs are often utilized but also pose several issues. For example, the duration of cold provided by ice or gel packs is limited, where, if extended periods of therapy are desired, the user must either use a very large pack, or replace the pack periodically. Further, it is difficult to control the temperature of such packs. For example, if the pack is simply applied to a patient, the fluid in the pack immediately adjacent the user may warm, requiring the user to shake or massage the pack to maintain a constant cooling temperature. These options can be worn and allow the user to ambulate, but do not involve circulating water, which gives a more consistent and constant temperature.

In physical therapy in-clinic applications, there are conventional electronic cold therapy devices that are heavy and bulky. Such devices require AC wall-socket power so they are not meant to be worn on the patient's body to permit freedom to ambulate.

SUMMARY OF THE INVENTION

The present invention in preferred embodiments is directed to a self-contained, mobile cold therapy device worn on a patient-user's body that enables the user to ambulate hands-free while receiving cold therapy to his or her injured region. The device includes a container including a thermally-insulated tank and a cold therapy liquid disposed in the tank. The preferred cold therapy liquid is below ambient temperature ice water.

The device further includes a cold therapy pad worn on the user's body, wherein the pad includes a thermal conduction surface engaging the user's body; at least one nipple protruding through the thermal conduction surface; a first air bladder disposed underneath the thermal conduction surface and engaging to the nipple, wherein the first air bladder is inflated to extend the nipple above the thermal conduction surface and is deflated to retract the nipple into the thermal conduction surface; a liquid bladder disposed underneath the thermal conduction surface; a second air bladder overlying and contiguous with the liquid bladder such that when inflated applies a compressive pressure on the liquid bladder.

The device further includes one or more liquid pumps disposed proximate or inside the container to circulate the liquid; one or more air pumps disposed proximate or inside the container; tubing interconnecting the liquid pump to the liquid bladder, and interconnecting the air pump to the first and the second air bladders; an electronic or digital controller and user interface disposed on the container and electrically wired to the air and liquid pumps; a battery pack powering the digital controller, the air pump, and the liquid pump; and a holder supporting the container on the user's body to enable the user to freely ambulate and with both hands free to engage in daily activity.

The cold therapy pad may be worn on the body and held in place using an elastic strap, swath, or wrap, or may be inserted into an orthopedic brace already prescribed for the user. The reciprocating nipple, pressed into the user's injured region, is driven by inflating and deflating the first air bladder. This reciprocating action of the nipple and/or air bladder helps massage the injured region and further reduces edema.

On board digital electronics monitor and control the air and liquid pumps to actuate one or the other or both. Thus, the device may have just the liquid therapy ongoing, or just air compression via the air bladder inflation, or both. Telemetry from the user and the device is collected by the digital electronics and sent through Wi-Fi, Bluetooth and the like to the internet, or to a smartphone or laptop. As such, the user or his or her care provider can monitor the cold therapy progress and provide feedback or administer control to the user or the device.

BRIEF DESCRIPTION OF THE DRAWINGS

FIG. 21 is a cold therapy device worn on a belt where the pad is attached to the user's injured wrist.

FIG. 22 is a cold therapy device worn on a belt where the pad is attached to the user's injured shoulder.

FIG. 23 is a cold therapy device worn on a belt where the pad is attached to the user's injured elbow.

DETAILED DESCRIPTION OF THE PREFERRED EMBODIMENTS

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Conventional circulating water cold therapy devices in the marketplace are stationary. The patient has to sit and stay in place while getting cold therapy with these products.

The preferred embodiments of the present invention device are light enough in weight so it can be worn on the user's body for many hours regardless of the user's physical stature. Further, the present invention cold therapy device is worn on the user's body in a holder, freeing his or her hands for activity and allowing the user to ambulate, all the while enabling the user to receive cold therapy. Therefore, the user can go for a walk in the park, go shopping in a store, and do a multitude of other things where the user is not confined to a small area and his or her hands are free for activity while receiving cold therapy. The holder can be any desired type of holder or carrying device, such as, for example, a fanny pack, a backpack, a bottle holder, a belt, a sling, a fanny pack, or like holder that can be worn on the person of the user for freedom to ambulate.

Figure 1:
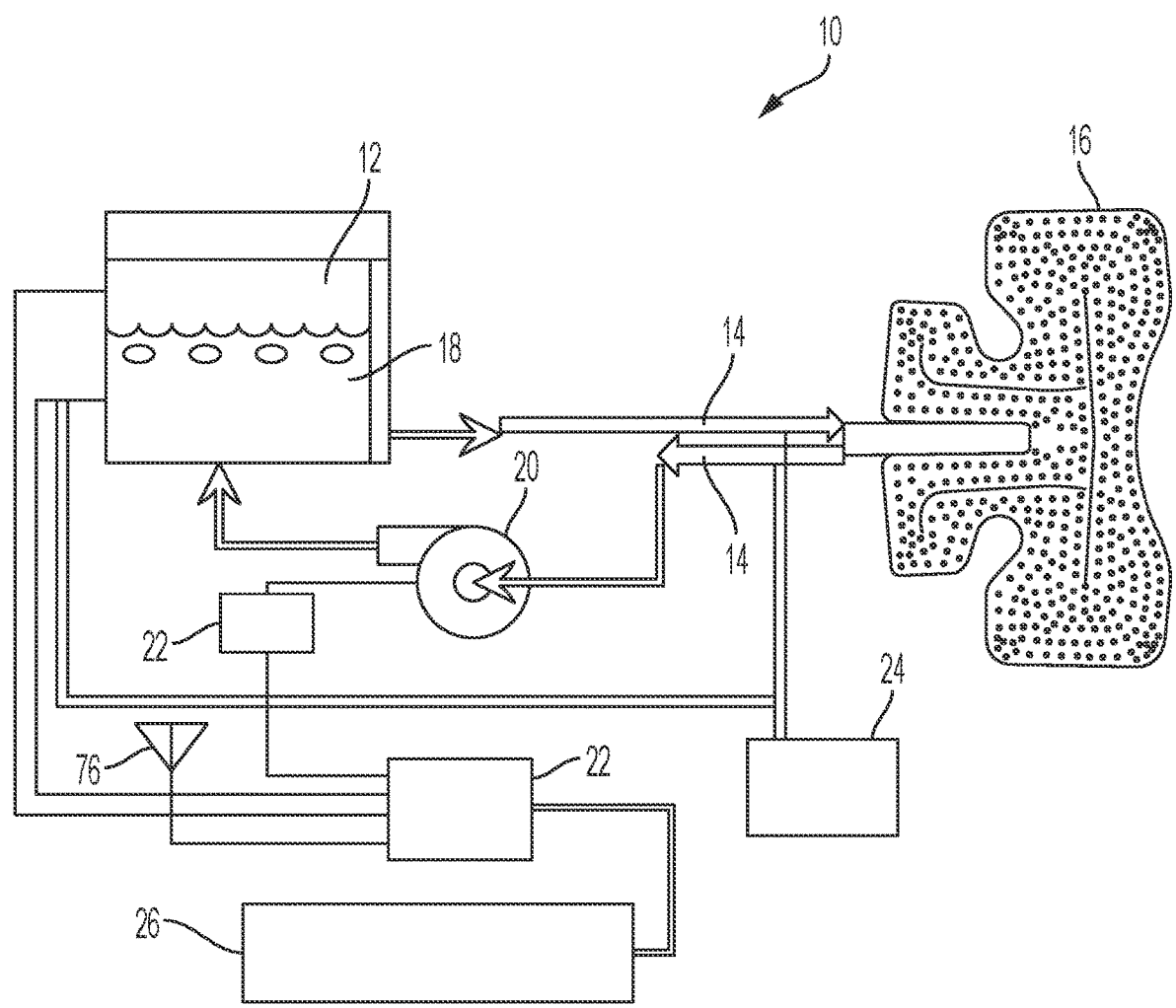
FIG. 1 is a schematic view of a preferred embodiment self-contained, mobile cold therapy device worn on a patient user's body.

FIG. 1 is a schematic representation of a preferred embodiment cold therapy device 10. The device 10 includes a housing or container 12 with preferably a thermally-insulated tank with tubing 14 in communication with the tank. A cold therapy fluid 18 such as below-ambient-temperature ice water resides inside the container tank 12 and is circulated to and from a cold therapy, thermal conduction pad 16 via the tubing 14.

Figure 24:
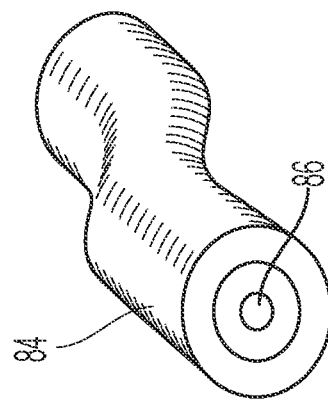
FIG. 24 is an end view of an alternative embodiment multi-lumen tube.

Separate tubes 14 are preferred as shown. Alternatively, the tubing may consist of multi-lumen tubing 84 as seen in FIG. 24. A single tube 84 with coaxial lumens 86 minimizes dangling tubing that may accidentally catch on a doorknob or the like. The multi-lumen tubing may also be several separate tubes held side-by-side inside a single tube. The tubing 14 is preferably thermally-insulated so the ice water carried within is not warmed up by the ambient environment.

The ice water 18 is circulated to the cold therapy pad 16 via the tubing 14 and back to the container tank 12 via an electric pump 20. The cooled ice water flow may be, for example, from about 33° F. to about 50° F. The mobile cold therapy device can work with circulating chilled ice water, salt water, alcohol, or like liquid, or some mixture thereof.

Figure 3:
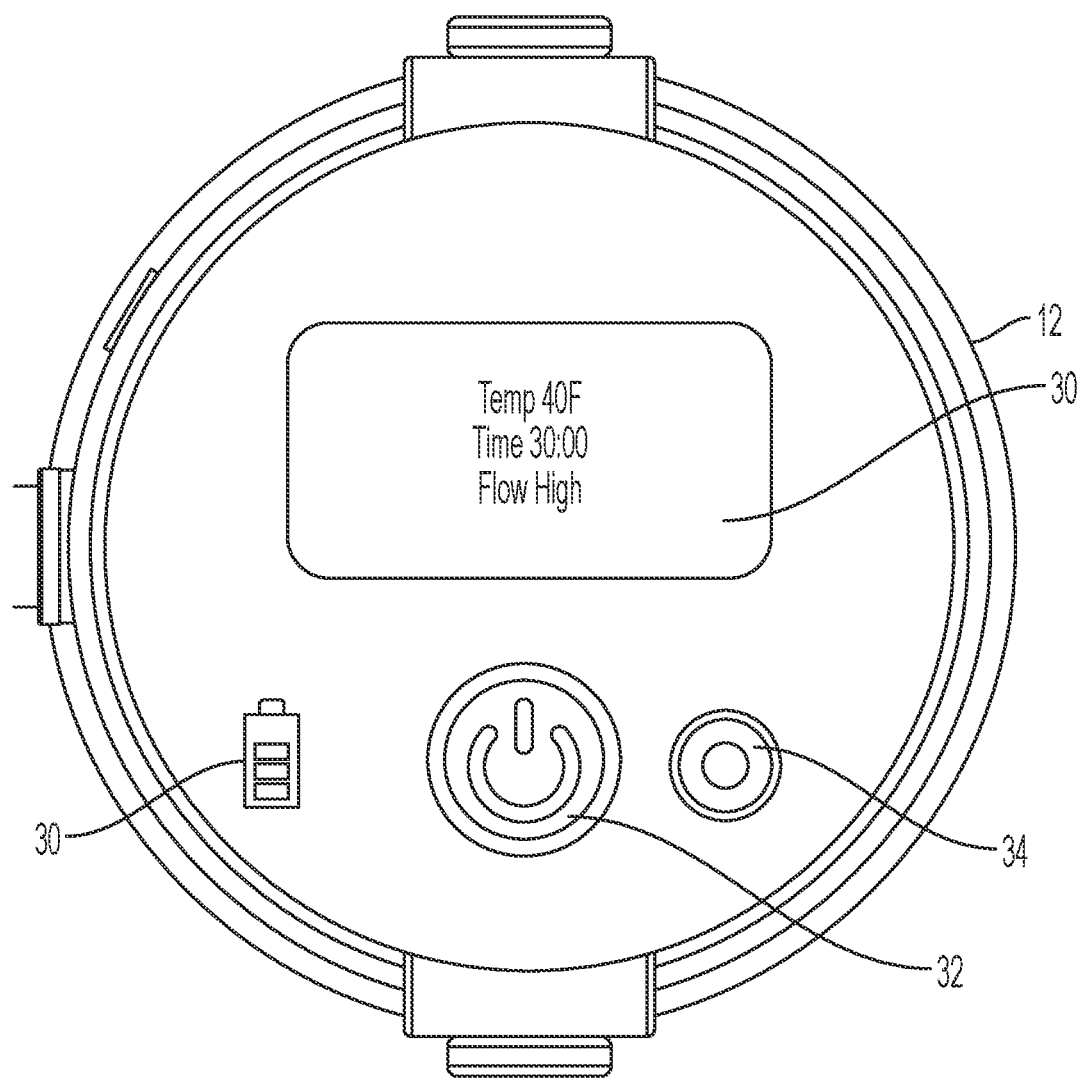
FIG. 3 is a plan view of a preferred embodiment display of the electronic interface such as a touch controls, telemetry display, operation buttons, battery charging port.

An electronic controller or microprocessor-based digital controller 22 monitors the water temperature via one or more temperature monitors 24 located in the water circuit. The digital controller 22 may further monitor and control the liquid flow rate, flow on/off, water flow duration with a timer, and cycling the liquid flow on, then off, then on, then off, etc. In FIG. 3, the digital controller 22 preferably includes an LCD or like display and/or touch screen 30 to inform the user of the device and patient's telemetry, and includes touch controls or physical pushbuttons or switches 32 for user interface to set up parameters for the device operation as described above, or to trigger pre-programmed subroutines for the cold therapy. A battery charging port and/or USB port 34 may be provided as well.

In some alternative embodiments, the present invention cold therapy device electronics can be programmed to account for the following preprogrammed modes: For example, a first mode where the user can press a start button and the pump runs for 30 minutes with a countdown timer. Firmware can be set up such that the pump cannot turn on again for 30 minutes to prevent over-cooling by the user. A second mode where the user can press the start button and the pump runs for 30 minutes with a countdown timer. Firmware is set up such the pump is unlocked to allow the user to run another 30-minute cycle without required time off between cycles. A third mode where the user can press start button and the pump runs for 20 minutes with a countdown timer, with or without a timer lock as discussed above with the first and second modes. Other modes may be pre-programmed or programmed by the user.

The digital controller 22 may include an internal antenna 76 (see FIG. 1) similar one found in a conventional smartphone (FIG. 4) for transmitting and receiving Wi-Fi, Bluetooth, or related RF signals. The device 10 can therefore communicate wirelessly with a smartphone, laptop, router, handheld remote control, etc. The USB port 34 may be used for data or control communication too. This further allows the cold therapy device 10 to be connected to the internet where a physical therapist, trainer, or orthopedist at a remote location may monitor or control the ongoing cold therapy session with a patient user.

Figure 4:
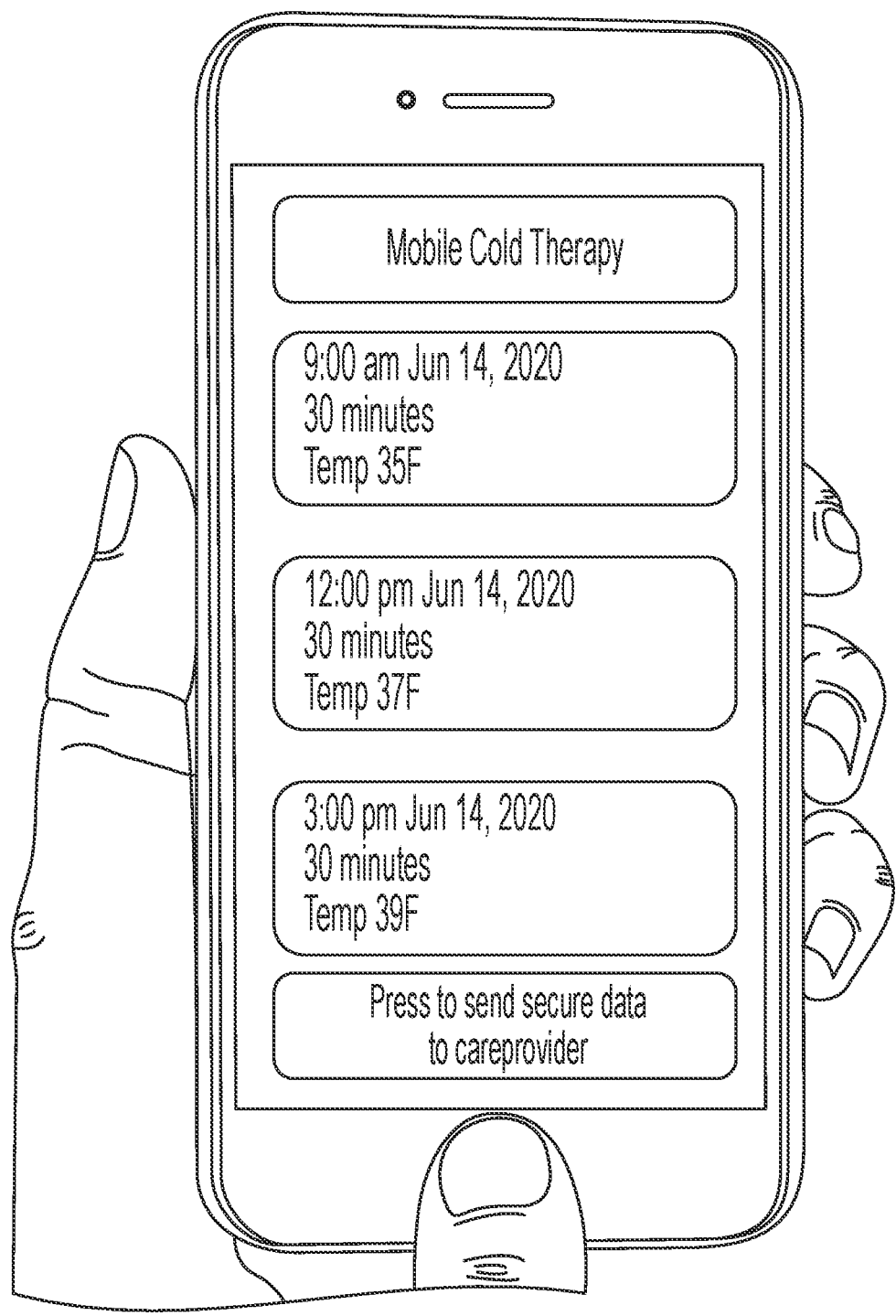
FIG. 4 shows a smartphone running an app wirelessly linked to the present invention cold therapy device.

In FIG. 4, a smartphone application can be used to communicate with the device's digital electronics and allow for secure data transmission. The user can use the cold therapy device for several days or weeks. Then when connected with the app, the patient use data, such as temp, time, date, cycle time, settings, or the like, can be transmitted through a wireless connection such as Bluetooth or Wi-Fi from the device to the cloud/internet. This allows the care provider with access to the data to monitor wound healing, recovery, physical therapy and the like. The care provider can monitor data and provide input to the patient via the app. For example, the case provider can send a message, such as, "Patient Name, we confirmed your prescribed cooling therapy sessions at 9:00 am and 12:00 pm. We see you missed your 3:00 pm session." Further, the user can also adjust settings of the device from phone application. The care provider can adjust cycle time and number of sessions per day. The care provider can send commands from a remote location through the cloud or a wireless connection to the cold therapy device or user's smartphone to enable or disable performance parameters. The cold therapy device can also send notifications to the user such as: "temperate is over 46 degrees F. and recommended to add ice to get the temperature back to target of 38-40 degrees F." In some embodiments, the device may be programmed to provide a cooling flow for a certain period of time, such as 20-30 minutes.

A battery pack 26 powers the pump 20, digital controller 22, and all other electronic components. The battery pack 26 may be removable and user replaceable. It may be recharged via the USB port 34. The battery pack 26 is preferably made from Lithium-Ion rechargeable batteries that can be plugged into a standard AC wall outlet to recharge when the device is not in use.

Figure 2:
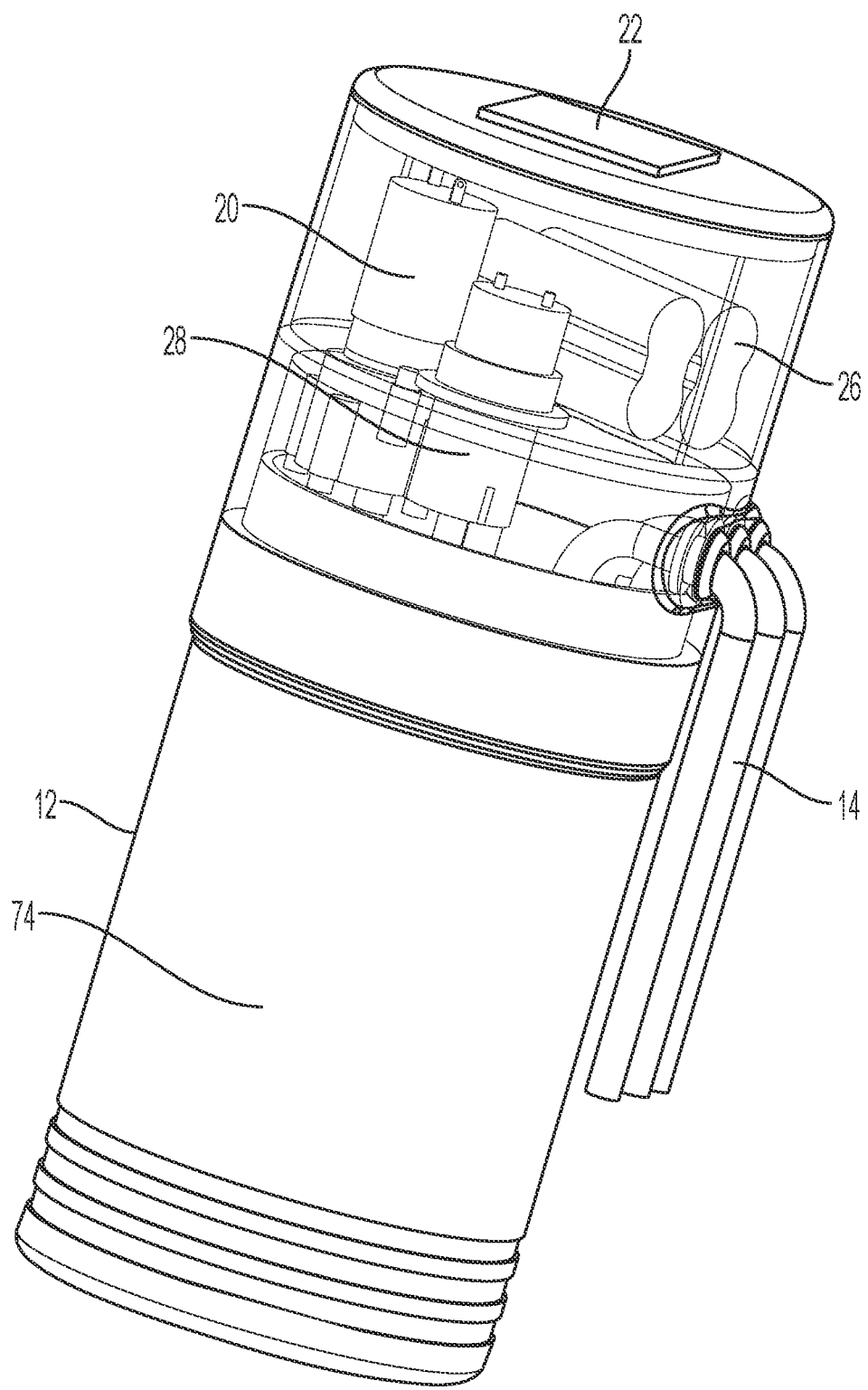
FIG. 2 is a preferred embodiment container showing arrangements internal to the container such as the air and liquid pumps, batteries, tubing, and electronic user interface and device controls.

FIG. 2 is a perspective view of a preferred embodiment housing or container 12. From the partial transparent view in FIG. 2, the container 12 has preferably a cylindrical shape where the top portion encloses the water/fluid pump 20, battery pack 26, and digital controller 22 located at the very top of the container 12. Inside the container 12 is a thermally insulated reservoir tank 74 holding the ice water or like cold therapy fluid 18. Tubing 14 is shown extending from the internal tank 74 of the container 12.

In a preferred embodiment cold therapy device, air is drawn from the ambient environment and pumped into an air bladder inside the pad 16 (described in detail below) to apply pressure to the user's injured tissue. Thus, the container 12 in FIG. 2 includes an air pump 28 that draws on ambient air and pumps that air through one of the tubes 14 into the pad 16 worn by the user. The fluid and air pumps 20, 28 may include mechanically operated valves, electronic valves, or electrostatic microvalves to regulate air or water flow rate; the valves may be controlled by the digital controller 22.

Figure 7A:
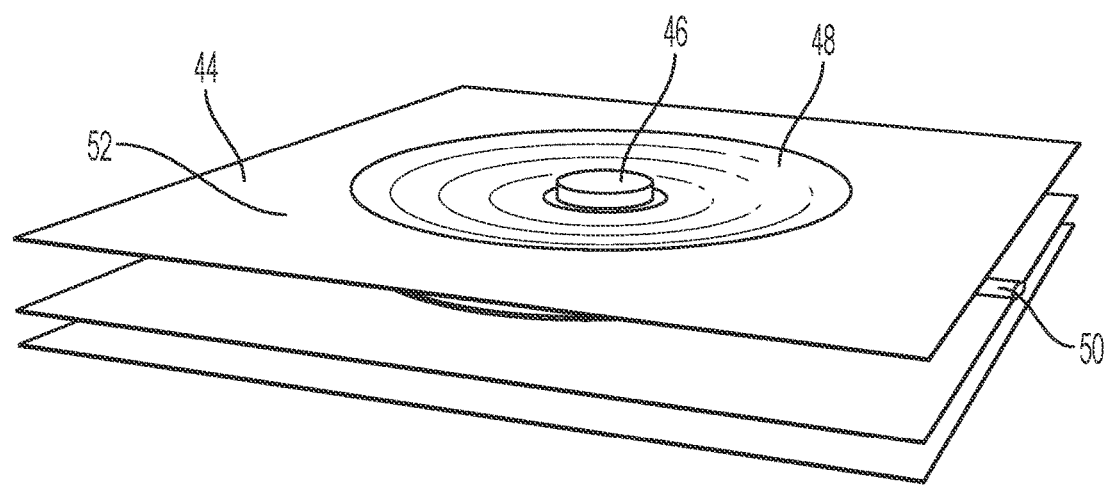
FIGS. 7(a) and 7(b) show the nipples in a retracted state on the thermal conduction surface of the pad.
Figure 7B:
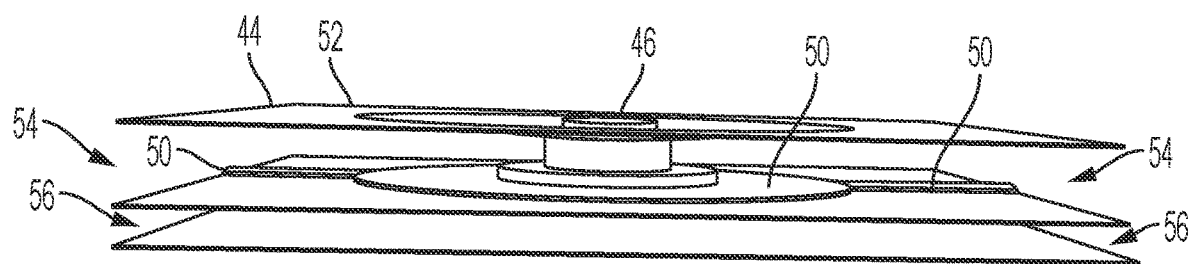
Figure 8A:
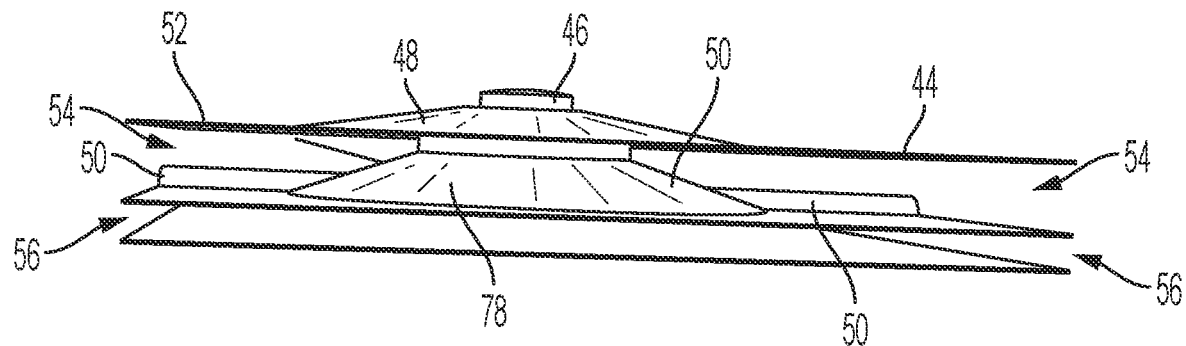
FIGS. 8(a) and 8(b) show the nipples in an extended state on the thermal conduction surface of the pad.
Figure 8B:
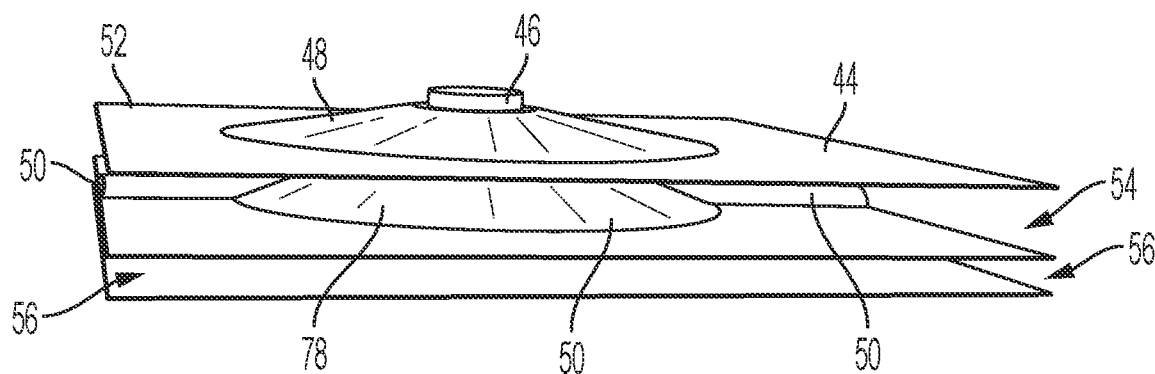

There are preferably four tubes 14 in the FIG. 2 embodiment: one tube to conduct cold water away from the container 12 to the cold therapy pad, one tube to return warm water back to the container 12 from the pad, one tube to force air to the air bladder inside the pad 16; and one tube (hidden from view) to force air to an outer air bladder 56 (FIG. 7(b), 8(b)). There may be more or fewer tubes than four, such as when a Y-connector is used, or dependent on the number of bladders used.

Figure 5A:
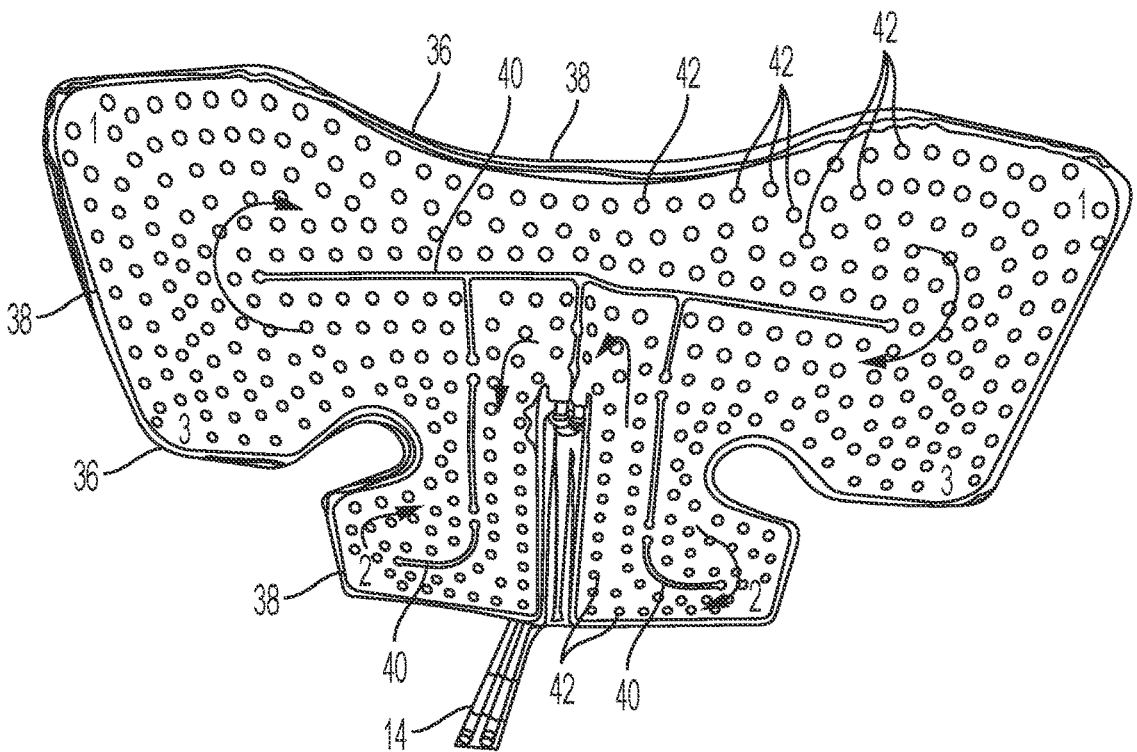
FIG. 5(a) shows a preferred embodiment cold therapy pad, specifically the thermal conduction surface facing the patient's injured region.
Figure 5B:
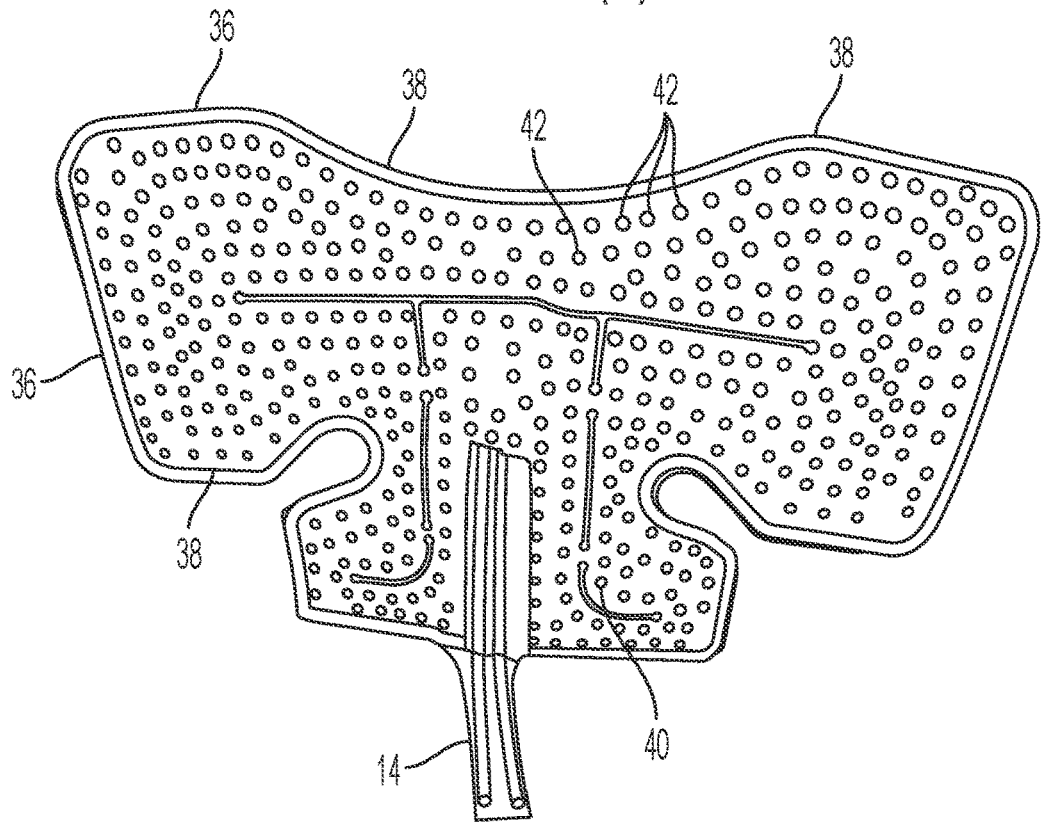
FIG. 5(b) is the backside of the pad shown in FIG. 5(a).

FIG. 5(a) shows a preferred embodiment thermal conduction pad 36 spread open to expose the patient's skin-facing, thermal conduction contact surface of the pad. FIG. 5(b) is the reverse side of pad 36 shown in FIG. 5(a). The reverse side is preferably at least partially covered by hook-and-loop fasteners for attachment of stays and/or a buffer sheet described below. There are two tubes 14 connected to the pad 36 to circulate chilled water into and out of the pad. The pad 36 has preferably two layers forming a hollow bladder where the layers are RF, laser, and/or heat welded together along its outer periphery 38, internal linear seams 40, and internal spots 42. The outer periphery weld 38 encloses the cold liquid therein. The internal linear seam welds 40 and internal spot welds 42 guide the liquid along a flow path and minimize the chance for the liquid not reaching any empty pockets inside the liquid bladder. The liquid or ice water flow path is represented by the arrows in FIG. 5(a).

Figure 6:
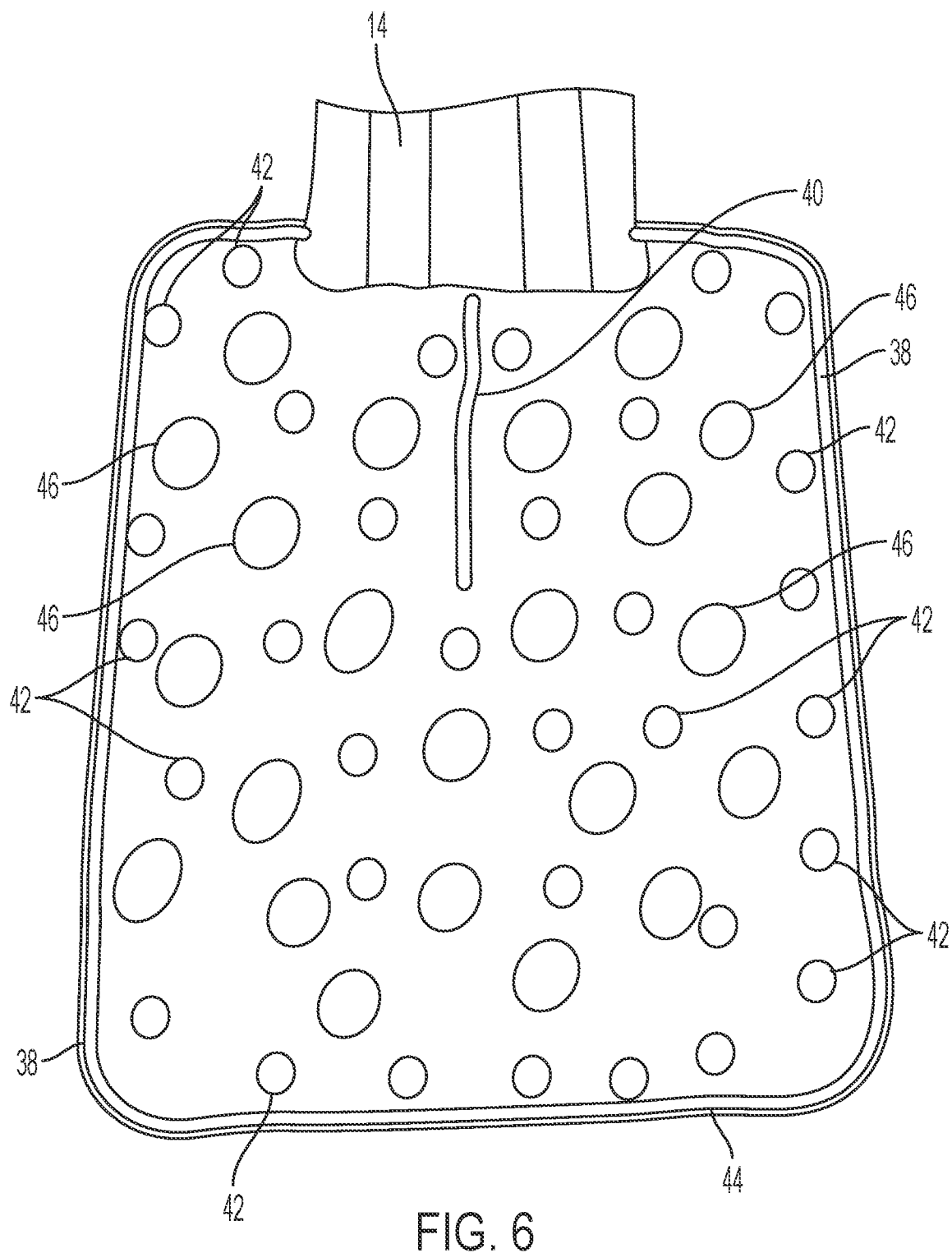
FIG. 6 is an exemplary embodiment pad that incorporates nipples.

FIG. 6 is a plan view of an alternative embodiment pad 44 revealing the patient's skin-facing thermal conduction surface. In this embodiment, the pad 44 includes the welded outer periphery 38 that creates one or more sealed bladders, and an internal linear seam 40, and a plurality of internal spot welds 42 as used in the FIG. 5 embodiment. This embodiment includes a plurality of protruding buttons, stubs, or nipples 46 arranged around the internal area of the pad 44. The nipples 46 are preferably round or bulbous, have a solid or hollow core, and are made from a soft or semi-rigid polymer such as polyurethane, or a metal or ceramic material, or any combination thereof.

The nipples 46 are activated by an inflatable air bladder 50 (see FIGS. 8(a), 8(b)) that drives the nipples 46 from underneath to protrude toward the patient's injured region. Deflating the bladder 50 retracts the nipples 46 back into the pad 44. By cyclically extending and retracting the nipples 46 against the user's injured region, the cold therapy device enhances the massaging and "milking effect" to further reduce edema.

FIGS. 7(a), 7(b), 8(a), and 8(b) are cross-sectional views of one nipple 46 from the pad 44 depicted in FIG. 6. FIGS. 7(a) and 7(b) specifically show the patient's skin-side, thermal conduction surface 52 of the pad 44 when the nipple 46 is retracted into a circular area 48 that forms a concave recess in that inner, thermal contact surface 52. The area 48 is preferably circular to help form a recess (or dome), but may be a polygon or an irregular shape. The thermal conduction surface or layer 52 is preferably made from a polymer sheet with some elasticity or resilience such as polyurethane. When the air bladder 50 underneath the nipple 46 is deflated as shown, the nipple 46 retracts into a lower position inside the (now concave) area 48 and sits flush, slightly below, or slightly above the thermal conduction surface 52 of the pad 44, as seen in FIG. 7(b). Underneath the surface 52 is the liquid bladder 54 conducting the flow of cold therapy fluid.

As best seen in FIGS. 7(a), 7(b), 8(a), 8(b), the liquid bladder 54 is preferably coextensive with the air bladder 50 so the air bladder 50 does not intrude or occupy too much surface area used by the thermal conduction surface 52. In a preferred embodiment, the nipple air bladder 50 is enclosed inside the liquid bladder 54.

FIGS. 8(a) and 8(b) show the air bladder 50 inflated under pressure, so the nipple 46 is extended from the now convex dome at the circular area 48. The liquid bladder 54 and distended air bladder 50 are more clearly visible in FIGS. 8(a) and 8(b). The distended air bladder 50 may include its own convex dome 78 that helps push the nipple 46 farther outward, protruding into the user's injured region. When the air pressure is lowered by turning off the air pump 28 or exhausting out from the bladder 50, then the nipple 46 retracts back into the circular area 48, which itself reverts back to its concave condition as shown in FIGS. 7(a), 7(b).

The inflated dome 78 in the air bladder 50 is likewise deflated. Cycling the air pressure inside the air bladder 50 causes the nipple 46 to extend and retract thereby milking the edema in the patient's injured region.

Figure 25:
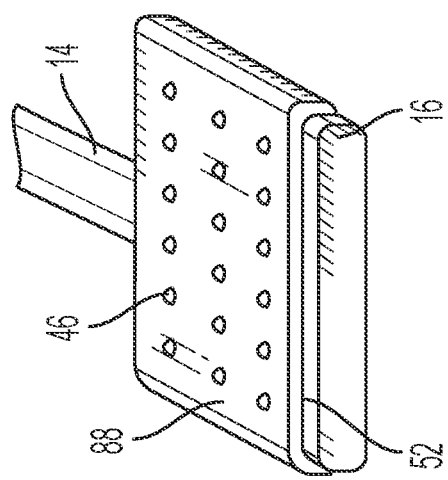
FIG. 25 shows a buffer sheet disposed on the thermal conduction surface of the pad that contacts the patient's skin.

As best seen in FIG. 25, a thin, sterile or non-sterile, buffer sheet 88 may be applied covering the skin-contacting, thermal conduction surface 52 and the nipples 46 of the cold therapy pad 16, 36, 44, 60. The preferred embodiment buffer sheet 88 is folded over at the outer periphery of the pad and secured by hook-and-loop fasteners on the pad. The removable buffer sheet 88 thus slightly insulates or buffers the thermal conduction surface 52 from the user's skin to minimize possible freeze burns to the user, while still allowing the cold therapy and reciprocating nipples 46 to function normally.

For illustration purposes in FIGS. 7(*a*), 7(*b*), 8(*a*) and 8(*b*), just "underneath" the liquid bladder 54 and air bladder 50 is an optional second air bladder 56. To clarify orientation of things in the drawings, as worn on the user's body, the nipples 46 and thermal conduction surface 52 face inward toward the patient's injured region, and the second air bladder 56 is the outer-most bladder. Therefore, this second, outer air bladder 56 when inflated exerts a compressive pressure on the liquid bladder 54 and nipples 46 urging both toward the user's injured region. The second air bladder 56 may be inflated and deflated in synch with the air pressure-driven reciprocating nipples 46 to enhance milking the edema. Also, the liquid bladder 54 may be drained so there is no cold therapy, while only the second air bladder 56 is used for the patient's physical therapy.

According to the above exemplary embodiment, the nipples 46 are well integrated into the thermal conduction surface 52 and require minimal surface area so as not to diminish the cold therapy function. The nipples 46 when not in use do not disturb the thermal conduction surface's contact with the patient's injured region. Further, the nipples may be made from a thermal conducting material so that when chilled by the liquid they also conduct cold to the patient's skin.

Figure 9:
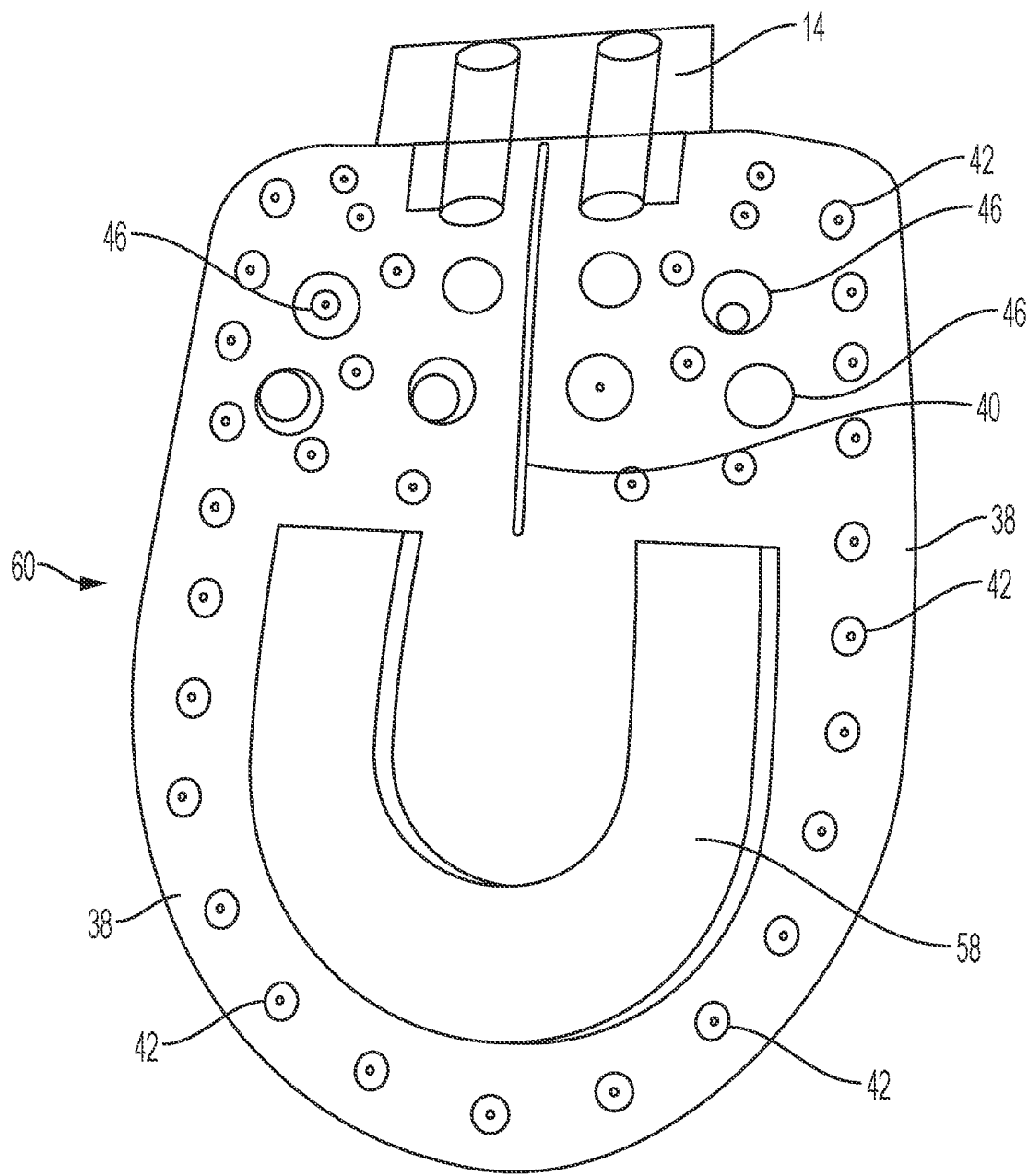
FIG. 9 shows an alternative embodiment pad having an additional U-shape air bladder disposed inside the pad.

FIG. 9 is a plan view of the thermal contact surface of an alternative embodiment cold therapy pad 60. Similar to the embodiment depicted in FIG. 6, the pad 60 has a welded peripheral seam 38 creating a sealed, liquid-carrying bladder therein where the cold therapy liquid is conducted via inlet and outlet tubing 14. The pad 60 includes a welded straight seam 40 and a plurality of spot welds 42 to control and distribute liquid flow inside the bladder. The shape of the pad 60 is different, perhaps for better fitment to, for example, the ankle area, or for an injured patella or knee region.

Also, the FIG. 9 pad 60 includes an additional U-shaped air bladder 58 acting as a single nipple that surrounds the malleolus of the ankle to further massage the edema from its most concentrated region. The U-shaped bladder 58 may be disposed inside the pad 60 as shown, or may be located on top of the thermal contact surface 52 in an alternative embodiment. The U-shaped air bladder 58 is inflated along with the nipple actuation by air pump 28. Other bladder shapes aside from the U-shape are contemplated for different body parts. Thus, more than one air bladder may be incorporated into pad 60. These additional air bladders 58 operate preferably in unison with the plurality of nipples 46 to exert compressive pressure on the liquid bladder 54, the user's injured region, or both. Alternatively, various sections of nipples may be driven separately by a plurality of separate air bladders as coordinated by the digital controller 22.

Figure 26:
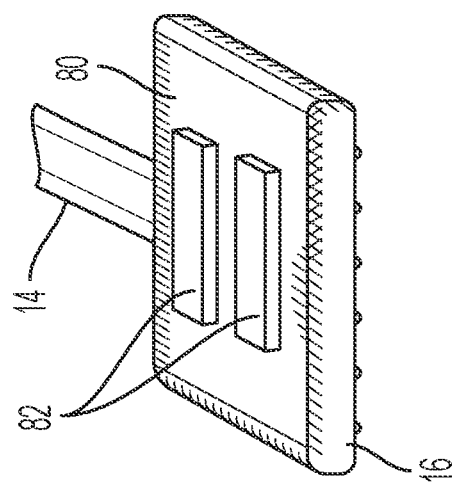
FIG. 26 shows malleable stays attached to the exterior of the pad.

FIG. 26 shows the pad 16 in an alternative embodiment having an outer surface 80 facing away from the user's skin that includes hook-and-loop fasteners. One or more stays 82 are attached to the outer surface 80 via the hook-and-loop fasteners. The semi-rigid stays 82 are preferably malleable to give shape to the pad 16 to conform to the injured body part; the stays 82 retain their shape after the user or physical therapist imparts that shape by hand. Examples of stay 82 sizes include a 1"×3" stay for smaller pads used for wrists, or a 1"×5" stay for larger pads used for the back, arm, shoulder, knee, or leg.

Figure 10:
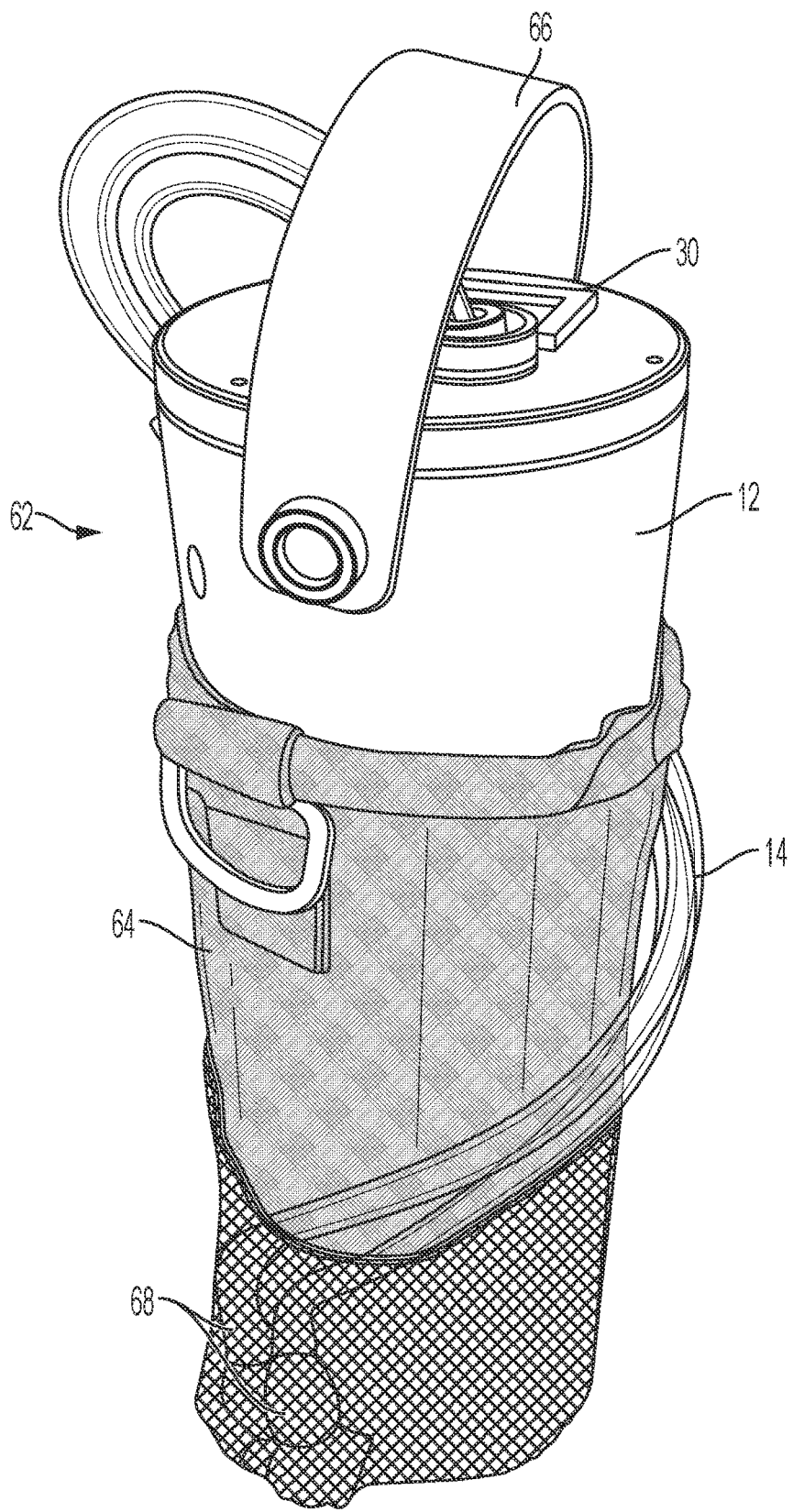
FIG. 10 is an alternative embodiment cold therapy device having a cylindrical form and held inside a holder.

FIG. 10 shows an alternative embodiment cold therapy device 62 with a handle 66 at the top of a container 12. The container 12 includes within the interior a thermally insulated liquid tank, control electronics, battery pack, and tubing 14 leading to a cold therapy pad (not shown). The container 12 is carried by a holder 64 to make the device 62 portable. At the distal ends of the tubing are leak-proof tubing interconnects 68 such as snap fittings, quick connects, screw fittings or the like to connect to more tubing sections. The tubing interconnects 68 are leak proof and do not require tools to join or disconnect. Therefore, the overall length of the tubing 14, may be adjusted by the user adding or removing sections of tubing via these interconnects 68.

Figure 11:
FIG. 11 is a perspective view of the cold therapy device held inside a sling holder and worn on the body of a user where the user can ambulate hands free.

FIG. 11 shows the cold therapy device 62 supported on the user's body by the holder 64 with a sling. The device 62 is small and light enough to be carried comfortably on the body, and he or she can ambulate hands-free without being tied to an AC wall socket. Therefore, the entire device 62 including insulated water tank (including cooling fluid), batteries, electronics, etc. as worn on the body ranges from approximately 5-15 lbs., most preferably about 8-10 lbs. based on empirical observations, and may be as low as about 3 lbs. or as high as about 20 lbs. depending on desired product parameters, patient body mass and anatomy, and duty cycle needed for the desired cold therapy. To fulfill the preferred parameters, the air pump and water pump are electrically driven, consuming approximately 0.5 W-15 W of power, and weighing less than approximately ½ lb. each. The battery pack provides at least approximately 3200 milli-amp-hours of energy to power the pumps and electronics, and weighs less than one pound. The battery packs are adequate to supply power for multiple treatment sessions without recharging. The preferred volume of the liquid storage tank may range between approximately 0.25 liter to at least approximately 2 liters.

In alternative embodiments, larger liquid tanks, greater pump capacity, and more battery power are contemplated for equestrian applications or the like. The present invention device being self-contained and mobile may be worn or carried on the body of the horse to provide cold therapy to the animal without confining the animal to a stall or a barn.

Figure 14:
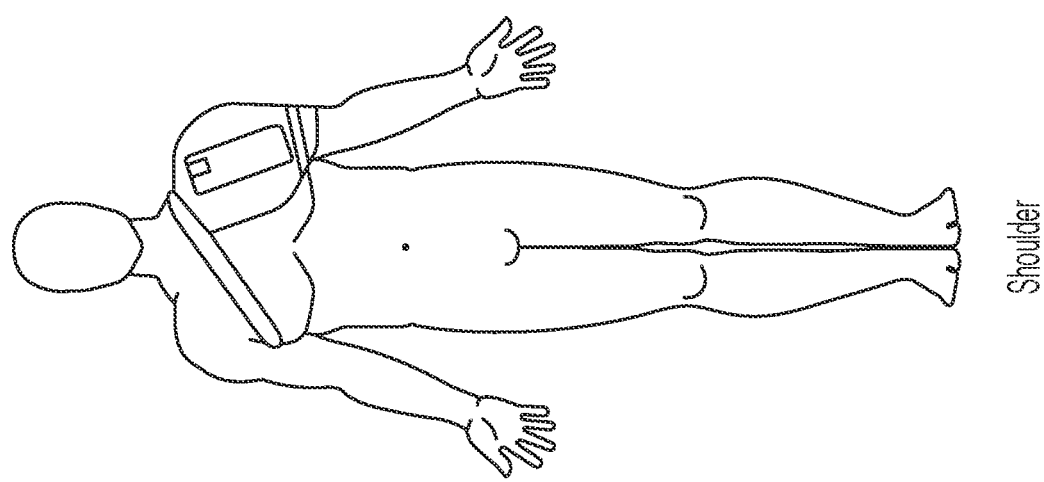
FIG. 14 is a cold therapy pad worn on a user's injured shoulder.
Figure 13:
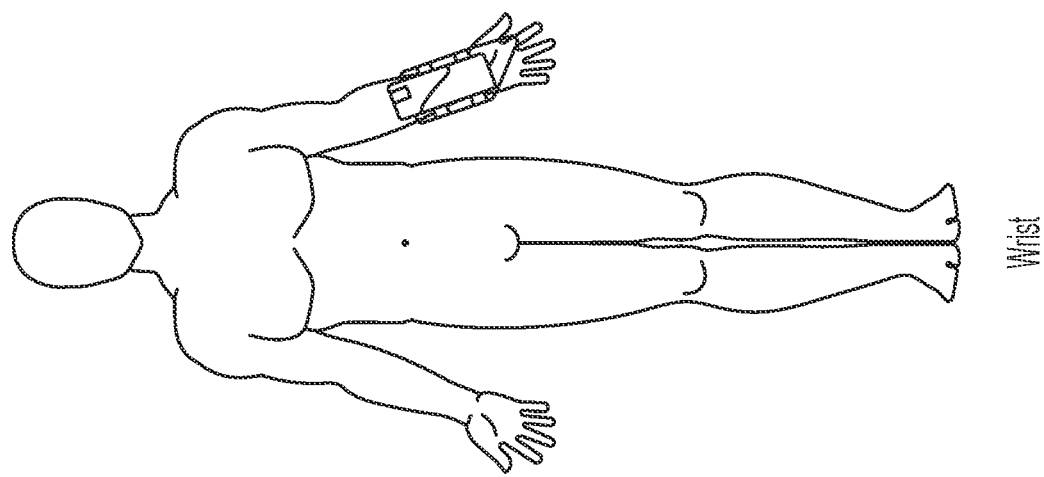
FIG. 13 is a cold therapy pad worn on a user's injured wrist.
Figure 18:
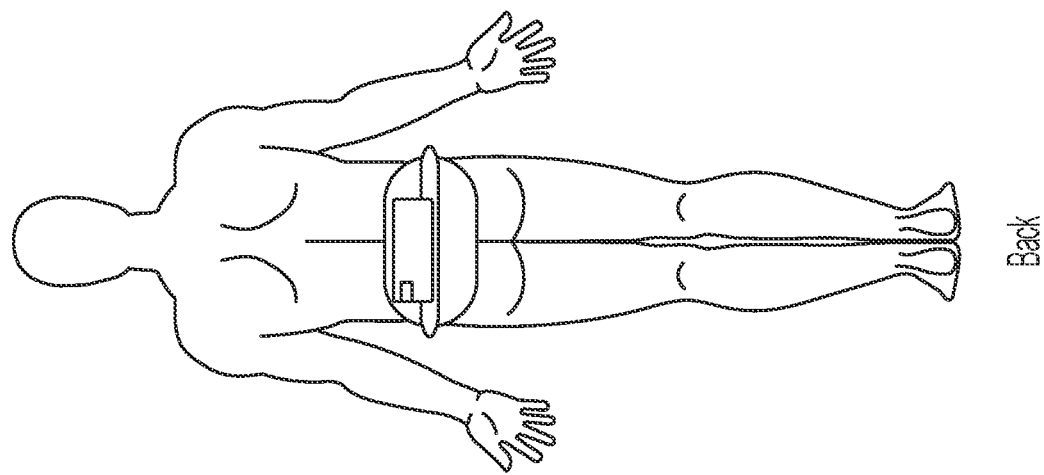
FIG. 18 is a cold therapy pad worn on a user's injured lower back.
Figure 17:
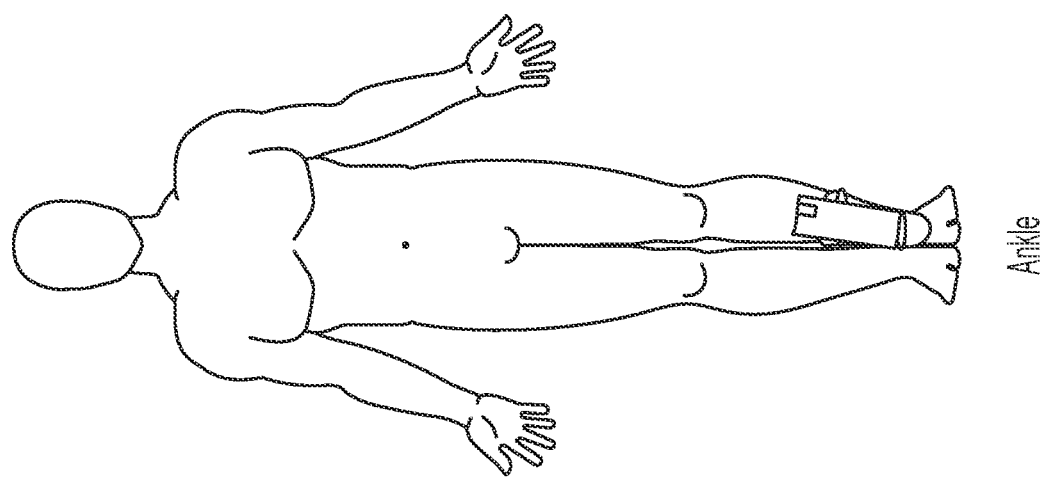
FIG. 17 is a cold therapy pad worn on a user's injured ankle.
Figure 16:
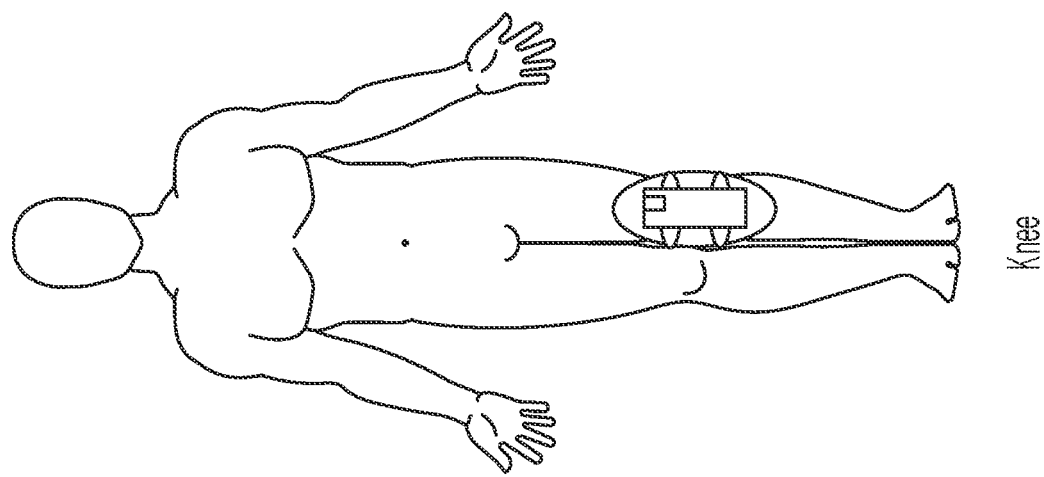
FIG. 16 is a cold therapy pad worn on a user's injured knee.

The holder 64 includes a pouch suspended by a sling strap as seen in FIG. 11. In an alternative embodiment, the pouch may be omitted so only an elastic strap is used to hold the device against the user's body. Further alternative embodiments use a garment-like fabric sheet swath or wrap similar to that shown in FIG. 14 to hold the cold therapy device against the user's body.

Figure 12A:
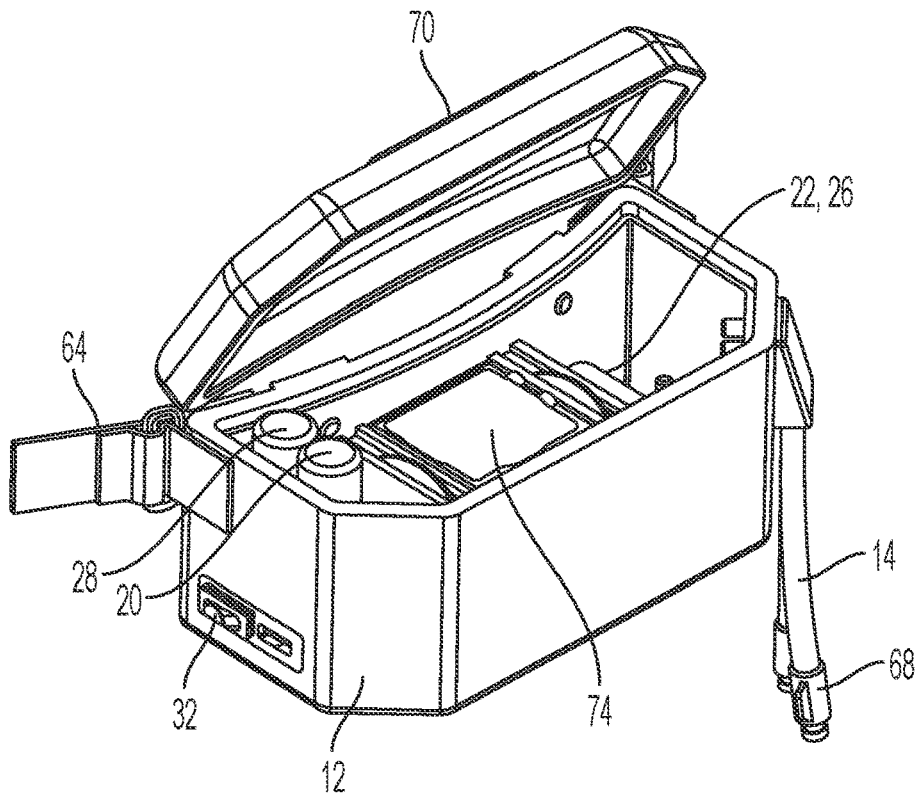
FIGS. 12(a) and 12(b) show an alternative embodiment cold therapy device where the container has a box form intended to be worn on a belt as with a fanny pack.
Figure 12B:
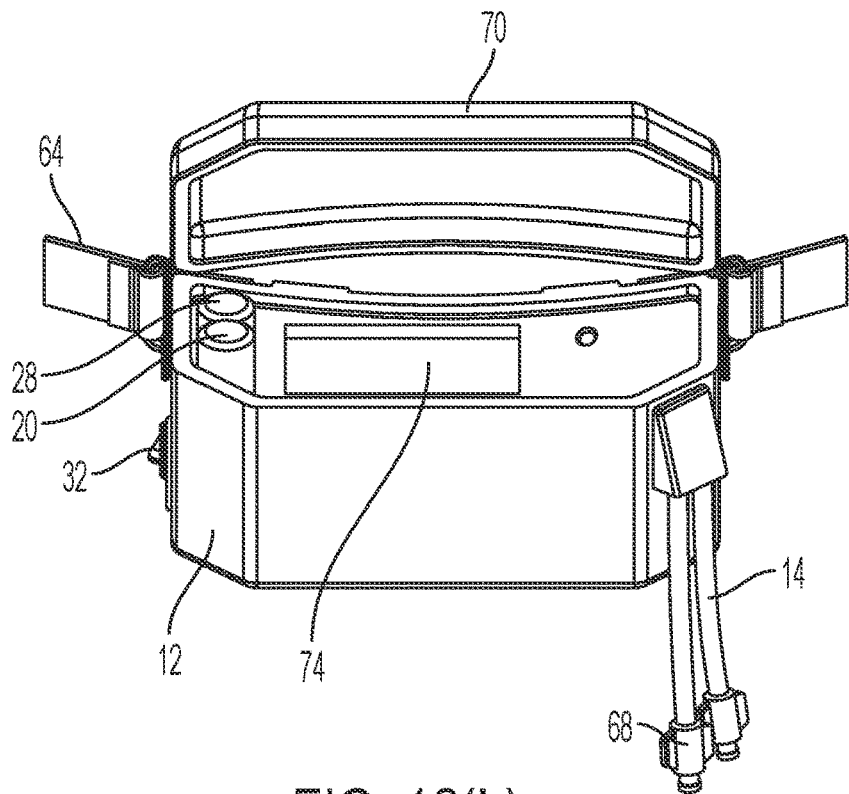
Figure 15:
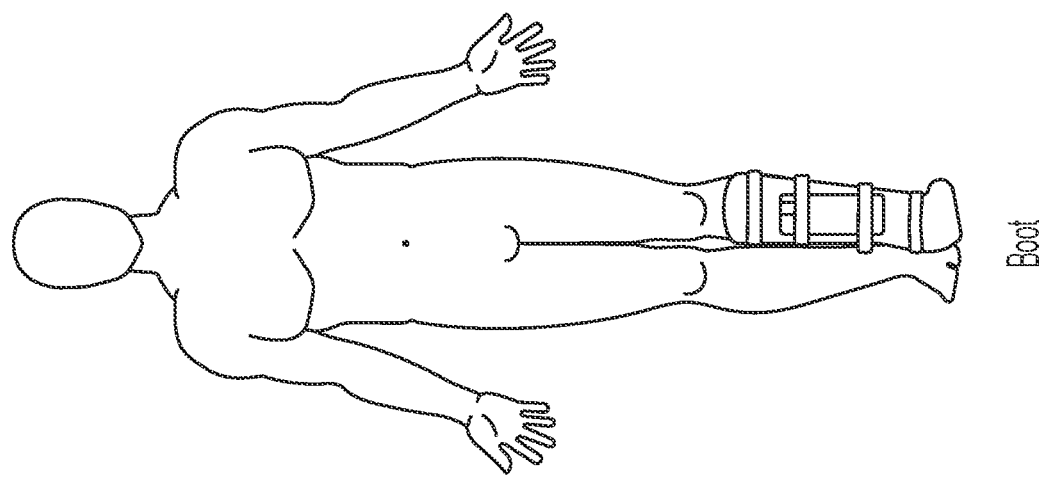
FIG. 15 is a cold therapy pad worn on a user's injured calf or ankle.

FIGS. 12(*a*) and 12(*b*) depict an alternative embodiment cold therapy device 70 in the form that can be worn as a fanny pack or attached to the user's waist. The holder 64 has a belt for attachment to the waist. The device 70 includes the liquid and air pumps 20, 28 inside a container 12 with a thermally insulated tank 74 for the cold therapy liquid such as ice water. The digital controller 22 and battery pack 26 reside inside the device container 12 and a user operable control switch 32 is located on an exterior surface. Tubing 14 for conducting cold therapy liquid and/or compressed air extend from the device 70 with tubing fittings, quick connects, or interconnects 68 at the distal ends.

Figure 19:
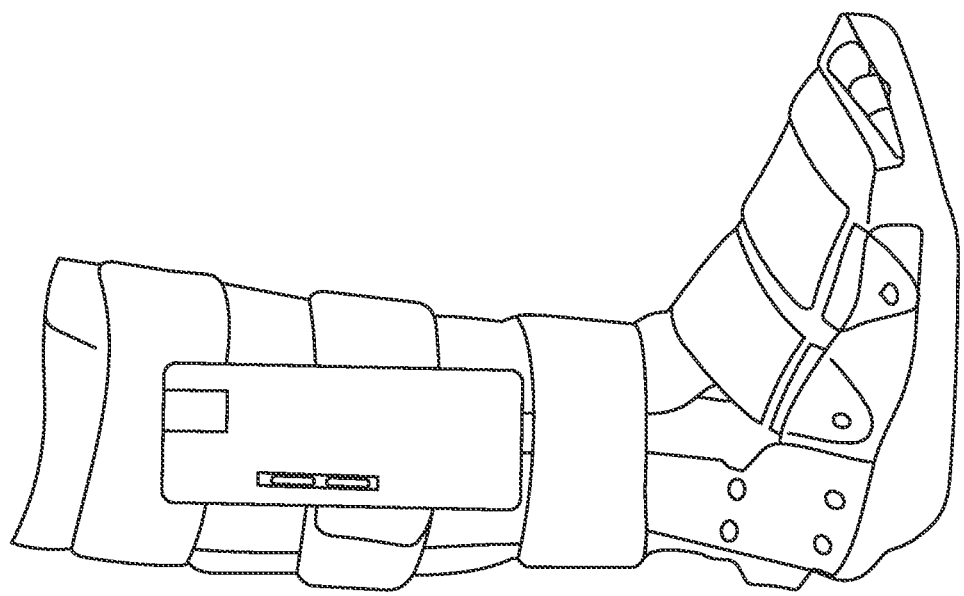
FIG. 19 is a cold therapy pad worn underneath a user's prescribed "space boot" ankle support.
Figure 20:
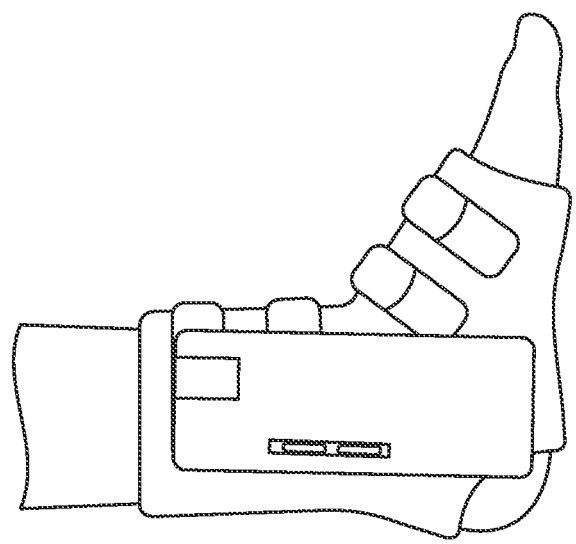
FIG. 20 is a cold therapy pad worn underneath a user's prescribed orthopedic ankle brace.

FIGS. 13-23 depict how the cold therapy pad may be incorporated into a pre-existing orthopedic brace or support prescribed for the user's injured wrist, shoulder, leg, knee, ankle, back, etc. FIG. 19 shows the cold therapy pad incorporated into a "space boot" type of ankle or foot orthosis. FIG. 20 shows the cold therapy pad incorporated into an ankle brace. FIGS. 21-23 show the fanny pack embodiment of the cold therapy device 70 worn about the waist. The cold therapy pad 72 is shown in FIGS. 21-23 worn on the user's wrist, shoulder, and elbow, as examples of different applications.

In some embodiments shown in FIGS. 13-23, the cold therapy device may attach directly to the orthotic brace to provide a cooling flow through a portion of the orthotic brace, or the device may be used with a cooling pad which may be attached to or placed under the orthotic brace. For example, if a user needs to have a joint immobilized for a required period of time due to an injury, cold therapy may be useful, but the immobilization orthosis may impede the cold therapy. With the present invention, a cold therapy pad, having chilled fluid flow therethrough, can be applied to the user prior to application of the immobilization orthosis. Thus, the user can wear or otherwise connect the tubing from the cold therapy device so a cooling flow is provided under the immobilization orthosis to simultaneously (1) reduce inflammation, (2) immobilize the injured joint, and (3) allow the patient to ambulate hands free.

In other alternative embodiments, the immobilization orthosis can have the cold therapy pad built in, where a cooling flow can be provided to the immobilization orthosis to cool the joint, for example, while maintaining immobilization of the joint. In some embodiments, the cold therapy device and the cooling pad can both be built into the orthotic brace. Of course, in any of the foregoing applications, the present invention cold therapy pad can be worn on the user's body without an orthotic brace.

Figure 27:
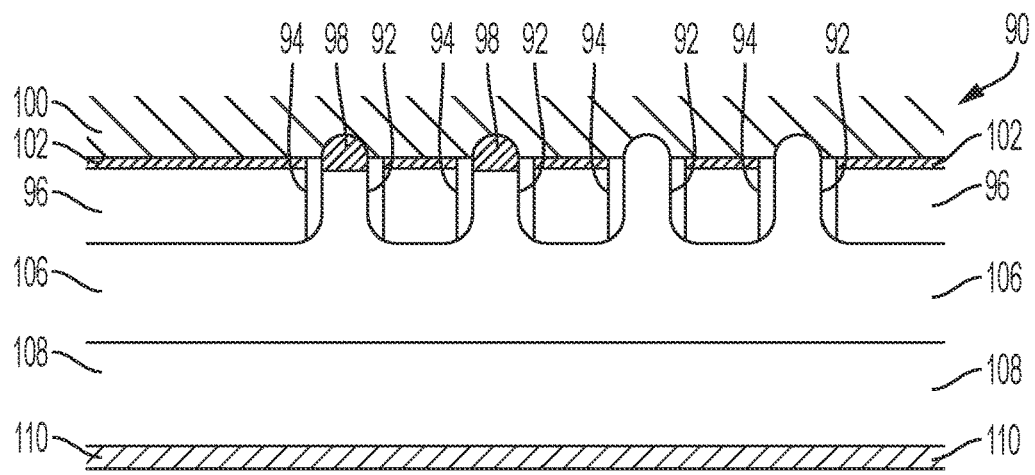
FIG. 27 is a cross-sectional diagram of an alternative embodiment pad showing an arrangement of the bladders with inflatable nipples passing through the liquid bladder.
Figure 28:
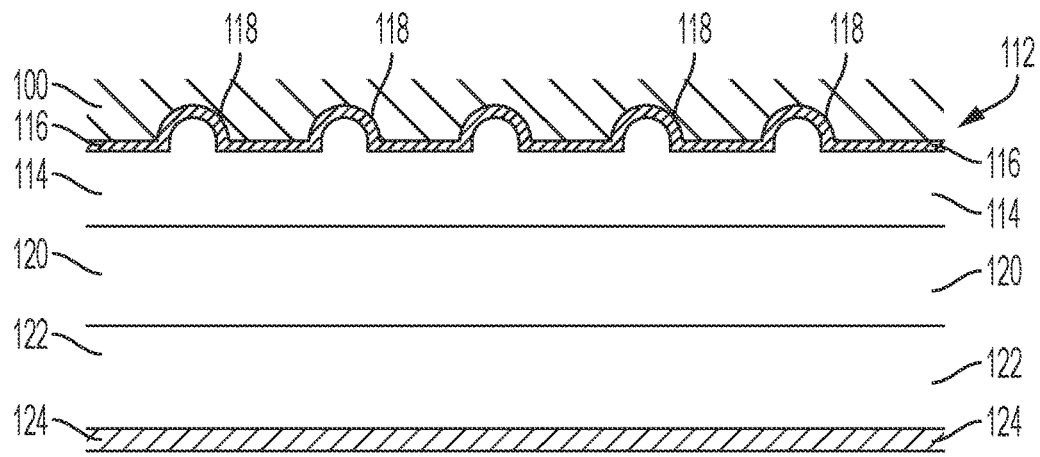
FIG. 28 is a cross-sectional diagram of another alternative embodiment pad wherein the inflatable nipples are directly abutting the wearer's skin.
Figure 29:
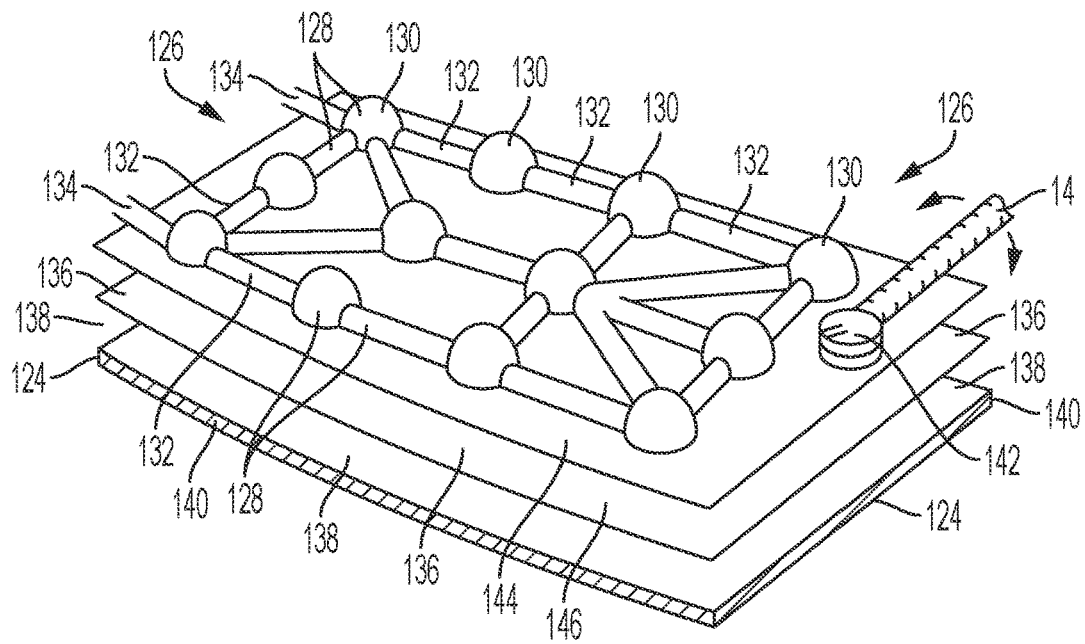
FIG. 29 is a diagram of yet another alternative embodiment pad wherein the inflatable nipples are interconnected by a network of channels that together form an inner air bladder.

FIGS. 27-29 depict alternative embodiment pads that have varying arrangements and constructions of inflatable fluid bladders and nipples. There are preferably a first, a second, and a third fluid bladders joined in overlying layers or laminates to form the pad. The inner-most fluid bladder has a skin-side surface, usually noted as the thermal conduction surface. The outer-most fluid bladder has an outer surface to receive optional hook-and-loop fasteners or like attachment means known in the art. The first, second, and third fluid bladders may be used to carry air or the cold therapy liquid (both being fluids), depending on the doctor's prescription or the patient's physical therapy needs.

For example, FIG. 27 is a cross-sectional diagram of an alternative embodiment pad 90 with inflatable nipples 92 that, when inflated as shown, pass through respective vertically-oriented tunnels 94 formed into an intervening bladder, which in this embodiment is a liquid/fluid bladder 96. One or more nipples 92 may be completely hollow or may have a thicker or a solid distal tip 98 as depicted in FIG. 27. The distal tips of the nipples 92 engage the patient's skin when the nipple is inflated. At the skin-facing side of the liquid bladder 92 is an optional thermal conduction membrane 102 which itself includes openings corresponding to the vertical tunnels 94 to enable passage of the nipples 92 therethrough. Abutting the liquid bladder 96 is the inner fluid air bladder 106, which is in communication with the nipples 92. Abutting the inner fluid air bladder 106 is an outer fluid air bladder 108. On an exterior surface of the outer fluid air bladder 108 are optional hook-and-loop fasteners 110 that enable attachment of the pad to the wearer's body.

FIG. 28 is a cross-sectional diagram of another alternative embodiment pad 112. In this embodiment, the first fluid bladder 114 contains air and it includes an optional thermal conduction membrane 166 with inflatable nipples 118. Abutting the air bladder 114 is a second fluid bladder 120 containing the cold therapy liquid. Abutting the second fluid bladder 120 is a third fluid bladder 122, which is the outer air compression bladder. An outer surface of the third fluid bladder 122 may include optional hook-and-loop fasteners 124. The contents of the first, second, and third fluid bladders may be interchanged between air and the cold therapy fluid in various alternative embodiments. For example, the first fluid bladder 114 with the nipples 118 may be filled with the cold therapy fluid. Then the second fluid bladder 120 may be inflated and deflated in cycles to pulse the nipples into the wearer's skin creating the massaging effect.

FIG. 29 is a diagram view of a "skeletal" pad embodiment. The pad 126 preferably includes an inner air bladder 128 that is constructed from inflatable nipples 130 that are in communication with a network of channels 132 that circulate pressurized air to and from the nipples 130. The channels 132 are in communication with one or more inlets and outlets 134 as supplied by the pump 20. The nipples 130, channels 132, or both may optionally be fabricated from a compliant, elastic material that when deflated, flattens out or loses most of its shape.

FIG. 29 shows the nipples 130 and channels 132 in their inflated state. The nipples 130 and network of channels 132 when inflated rise above the surface of the next adjacent bladder, in this instance, the cold therapy bladder 136. In a preferred embodiment, the nipples 130 and channels 132 are formed onto the surface of the cold therapy bladder 136. Then directly abutting the cold therapy bladder 136 is an outer air bladder 138. An outside surface of the outer air bladder 138 may optionally include hook-and-loop fasteners 140.

FIG. 28 also provides a representative cross-sectional view of the embodiment shown in FIG. 29 with the inner air bladder 128 (114 in FIG. 28) having the network of channels 132 and inflatable nipples 130 (118 in FIG. 28). The difference is that the inner air bladder may be formed by a unitary-chamber bladder with nipples thereon such as with prior embodiments, or may be formed from a lattice or network of channels with nipples as in FIG. 29.

In still another alternative embodiment, the inner air bladder 128 with the nipples and network of channels from FIG. 29 would replace the inner air bladder 106 in FIG. 27. The nipples 130 (FIG. 29) would pass through respective tunnels 94 in the cold therapy bladder 96 (FIG. 27). To be sure, the inner air bladder 128 of FIG. 29 may be used in place of any inner air bladder described in any of the aforementioned embodiments.

The wall thicknesses and internal capacity of each bladder and the size and shapes of the nipples are presented in the diagrams only for ease of illustration. They do not necessarily represent the structures' true shapes and relative sizes and thicknesses.

FIG. 29 further depicts an optional port 142 used to connect the fluid supply tubing 14 to any of the first, second, or third fluid bladders. In this embodiment, the second fluid bladder/cold therapy bladder 136 includes relatively flat top and bottom surfaces 144, 146 and the port 142 is attached to the top surface 144. The tubing 14 is in communication with the interior of the cold therapy bladder 136 via port 142. The port 142 preferably includes a swivel so that the tubing 14 may rotate (arrows) in a plane parallel to the top or bottom surfaces 144, 146. This azimuth-rotating port feature minimizes the tubing 14 from bunching, kinking, or twisting as the pad is moved along with the wearer's body when he or she engages in physical activity.

While particular forms of the invention have been illustrated and described, it will be apparent that various modifications can be made without departing from the spirit and scope of the invention. It is contemplated that disclosed embodiments and their components may be combined with other disclosed embodiments and their components.

What is claimed is:

1. A self-contained, mobile cold therapy system circulating a cold therapy fluid and air, worn on a user's body hands-free that enables the user to freely ambulate, comprising:
   a tank holding the cold therapy fluid;
   a pad worn on the user's body, wherein the pad includes:
      a first fluid bladder having a thermal conduction membrane including inflatable nipples that when inflated engage the user's body, and are in communication with a network of channels;
      a second fluid bladder abutting the first fluid bladder;
      a third fluid bladder having an outer surface, wherein the third fluid bladder abuts the second fluid bladder;
      means for attachment disposed on the outer surface of the third fluid bladder;
   a pump circulating fluid in at least one of the first, second, and third fluid bladders;
   tubing interconnecting the pump and tank to at least one of the first, second, and third fluid bladders;
   electronics controlling the pump and powered by a battery; and
   a holder supporting at least one of the tank, pump, and electronics on the user's body.

2. The self-contained, mobile cold therapy system of claim 1, wherein at least one of the fluid bladders includes a top surface and a bottom surface and the tubing is in communication with the fluid bladder and is attached to at least one of the top surface and the bottom surface.

3. The self-contained, mobile cold therapy system of claim 2, wherein the at least one of the top surface and the bottom surface includes a fluid port that swivels and is connected to the tubing enabling the tubing to rotate relative to the fluid bladder.

4. The self-contained, mobile cold therapy system of claim 1, wherein the first fluid bladder includes air.

5. A mobile cold therapy pad for use with a self-contained, mobile cold therapy device worn on a user's body, the device having a tank containing a cold therapy fluid; a pump circulating the fluid and drawing ambient air; tubing interconnecting the pump to the pad; an electronic controller wired to the pump; a battery powering the electronic controller and the pump; a holder supporting the device hands-free on the user's body; the pad comprising:
   a first fluid bladder having a thermal conduction membrane including inflatable nipples that protrude from the first fluid bladder when inflated and engage the user's body;
   a second fluid bladder abutting the first fluid bladder at a surface opposite to the thermal conduction membrane; and
   a third fluid bladder having an outer surface, wherein the third fluid bladder abuts the second fluid bladder.

6. The self-contained, mobile cold therapy pad of claim 5, wherein at least one of the fluid bladders includes a top surface and a bottom surface and the tubing is in communication with the fluid bladder and is connected via a port on at least one of the top surface and the bottom surface.

7. The self-contained, mobile cold therapy pad of claim 5, wherein the first fluid bladder includes air.

8. The self-contained, mobile cold therapy pad of claim 5, wherein the first fluid bladder includes the cold therapy fluid.

9. The self-contained, mobile cold therapy pad of claim 5, wherein the first fluid bladder further comprises a network of channels in communication with the nipples.

10. A self-contained, mobile cold therapy device circulating a cold therapy fluid and air, worn on a user's body hands-free that enables the user to freely ambulate, comprising:
   a tank holding the cold therapy fluid;
   a pad worn on the user's body, wherein the pad includes:
      a first fluid bladder disposed adjacent a thermal conduction membrane, wherein the first fluid bladder includes a through-hole tunnel;
      a second fluid bladder disposed adjacent the first fluid bladder having at least one inflatable nipple passing through the tunnel in the first fluid bladder and the thermal conduction membrane;
      a third fluid bladder disposed adjacent the second fluid bladder;
      hook and loop fasteners disposed on an outer surface of the third fluid bladder;
   a pump circulating the fluid in at least one of the first, second, and third fluid bladders;
   tubing interconnecting the pump and the tank to at least one of the first, second and third bladders;
   electronics controlling the pump and powered by a battery; and
   a holder supporting at least one of the tank, pump, and electronics.

11. The self-contained, mobile cold therapy device of claim 10, wherein at least one of the first, second, and third fluid bladders includes a top surface and a bottom surface and the tubing is in communication with the fluid bladder and is connected via a swiveling port on at least one of the top surface and the bottom surface.

12. The self-contained, mobile cold therapy device of claim 10, wherein the first fluid bladder includes the cold therapy fluid.

13. The self-contained, mobile cold therapy device of claim 10, wherein the second inflatable bladder includes air.

14. The self-contained, mobile cold therapy device of claim 13, wherein the inflatable nipple includes a hollow interior that is in communication with the second inflatable bladder.

15. A self-contained, mobile cold therapy device circulating a cold therapy fluid and air, worn on a user's body hands-free that enables the user to freely ambulate, comprising:
   a tank holding the cold therapy fluid;
   a pad worn on the user's body, wherein the pad includes:
      a first fluid bladder having a plurality of at least partially hollow, inflatable nipples in communication with a network of channels;
      a second fluid bladder abutting the first fluid bladder;
      a third fluid bladder having an outer surface, wherein the third fluid bladder abuts the second fluid bladder;
   a pump circulating fluid in at least one of the first, second, and third fluid bladders;
   tubing interconnecting the pump and tank to at least one of the first, second, and third fluid bladders;

electronics controlling the pump and powered by a battery; and a holder supporting at least one of the tank, pump, and electronics on the user's body.

16. The self-contained, mobile cold therapy device of claim 15, wherein the first fluid bladder includes air.

17. The self-contained, mobile cold therapy device of claim 16, wherein the second fluid bladder includes the cold therapy fluid.

18. The self-contained, mobile cold therapy device of claim 16, wherein the second fluid bladder includes the cold therapy fluid and includes a plurality of vertical tunnels, and wherein the nipples of the first fluid bladder extend through the tunnels.

19. The self-contained, mobile cold therapy device of claim 15, wherein the network of channels and the nipples inflate and deflate together.

20. The self-contained, mobile cold therapy device of claim 15, wherein first fluid bladder network of channels and nipples rise above the surface of the second fluid bladder.

* * * * *